US010604655B2

(12) United States Patent
Williams et al.

(10) Patent No.: US 10,604,655 B2
(45) Date of Patent: Mar. 31, 2020

(54) ASPHALT PRODUCTS AND MATERIALS AND METHODS OF PRODUCING THEM

(71) Applicant: IOWA STATE UNIVERSITY RESEARCH FOUNDATION, INC., Ames, IA (US)

(72) Inventors: R. Christopher Williams, Ames, IA (US); Joseph Herbert Podolsky, Ames, IA (US); Eric W. Cochran, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 133 days.

(21) Appl. No.: 15/507,475

(22) PCT Filed: Aug. 31, 2015

(86) PCT No.: PCT/US2015/047810
§ 371 (c)(1),
(2) Date: Feb. 28, 2017

(87) PCT Pub. No.: WO2016/033605
PCT Pub. Date: Mar. 3, 2016

(65) Prior Publication Data
US 2017/0283615 A1    Oct. 5, 2017

Related U.S. Application Data

(60) Provisional application No. 62/046,105, filed on Sep. 4, 2014, provisional application No. 62/044,028, filed on Aug. 29, 2014.

(51) Int. Cl.
| C08L 95/00 | (2006.01) |
| C08K 5/05 | (2006.01) |
| C07D 493/04 | (2006.01) |
| C07D 493/00 | (2006.01) |
| C08K 5/1515 | (2006.01) |

(52) U.S. Cl.
CPC ............ *C08L 95/00* (2013.01); *C07D 493/00* (2013.01); *C07D 493/04* (2013.01); *C08K 5/05* (2013.01); *C08K 5/1515* (2013.01); *C08L 2555/24* (2013.01); *C08L 2555/64* (2013.01); *Y02A 30/333* (2018.01)

(58) Field of Classification Search
CPC ... C08L 95/00; C08L 2555/24; C08L 2555/64
See application file for complete search history.

(56) References Cited

U.S. PATENT DOCUMENTS

| 2,782,216 A | 2/1957 | Hayes et al. |
| 3,070,608 A | 12/1962 | Kuester et al. |
| 3,755,226 A | 8/1973 | Christiansen et al. |
| 4,597,799 A | 7/1986 | Schilling |
| 4,806,166 A | 2/1989 | Schilling et al. |
| 4,836,857 A | 6/1989 | Hopkins |
| 4,966,490 A * | 10/1990 | Hodson .................. E01C 19/16 118/103 |
| 5,023,282 A | 6/1991 | Neubert |
| 5,221,703 A | 6/1993 | Ostermeyer |
| 5,271,767 A | 12/1993 | Light, Sr. et al. |

(Continued)

FOREIGN PATENT DOCUMENTS

| CN | 101041574 A | 9/2007 |
| CN | 101694083 A | 4/2010 |

(Continued)

OTHER PUBLICATIONS

International Search Report and Written Opinion for Application No. PCT/US2015/047798 (dated Dec. 9, 2015).
Kim, Y.R., "Program Book of the 12th ISAP Conference on Asphalt Pavements," 12th ISAP Conference, Jul. 1, 2014, Raleigh, North Carolina.
Podolsky et al., "Investigation of Bio-derived Materials Including Isosorbide-based Materials as Bio-based Warm Mix Asphalt Additives," Poster Presentation ISAP 2014 Conference, Jun. 5, 2014, p. 1, Raleigh, North Carolina.
Preliminary Agenda and Abstracts of the 51st Petersen Asphalt Research Conference, Wyoming Conference Center (Jul. 16, 2014).

(Continued)

*Primary Examiner* — Renee Robinson
(74) *Attorney, Agent, or Firm* — Pepper Hamilton LLP

(57) ABSTRACT

The present invention relates to a method of producing an improved asphalt. The method involves providing an asphalt and providing a compound of formula (I), as described herein. The asphalt is mixed with the compound of formula (I) under conditions effective to produce an improved asphalt. Also disclosed are an asphalt product and a method of making asphalt material. The invention further discloses a method of producing an improved asphalt comprising providing a polymer modified asphalt and providing a compound of formula (IIa) or formula (II). The polymer modified asphalt is mixed with the compound of formula (IIa) or formula (IIb) under conditions effective to produce an improved asphalt, which is yet another aspect of the present invention.

12 Claims, No Drawings

(56) References Cited

U.S. PATENT DOCUMENTS

| | | | |
|---|---|---|---|
| 5,437,717 A | 8/1995 | Doyle et al. | |
| 5,473,000 A | 12/1995 | Pinomaa | |
| 6,797,753 B2 | 9/2004 | Benecke et al. | |
| 7,420,008 B2 | 9/2008 | Bloom | |
| 7,842,746 B2 | 11/2010 | Bloom et al. | |
| 7,951,766 B1 * | 5/2011 | Frenkel | C11D 3/43 510/365 |
| 7,951,862 B2 | 5/2011 | Bloom et al. | |
| 7,994,107 B2 | 8/2011 | Bloom | |
| 8,034,172 B2 | 10/2011 | Naidoo et al. | |
| 8,137,451 B2 | 3/2012 | Aerts et al. | |
| 8,198,223 B2 | 6/2012 | Bloom | |
| 8,198,224 B2 | 6/2012 | Bloom | |
| 8,257,483 B2 | 9/2012 | Aerts et al. | |
| 8,703,849 B2 | 8/2014 | Hagberg et al. | |
| 8,808,445 B2 | 8/2014 | Coe | |
| 8,926,742 B2 | 1/2015 | Coe | |
| 9,000,196 B2 | 4/2015 | Hagberg et al. | |
| 2002/0026884 A1 | 3/2002 | Raad | |
| 2004/0025745 A1 | 2/2004 | Freisthler | |
| 2005/0038147 A1 | 2/2005 | Andersen | |
| 2009/0137705 A1 | 5/2009 | Faucon Dumont et al. | |
| 2010/0034586 A1 | 2/2010 | Bailey et al. | |
| 2010/0040832 A1 | 2/2010 | Herbert | |
| 2010/0275817 A1 | 11/2010 | Williams et al. | |
| 2013/0022823 A1 | 1/2013 | Franks, Sr. | |
| 2013/0160674 A1 | 6/2013 | Hong et al. | |
| 2013/0171899 A1 | 7/2013 | Kalkanoglu et al. | |
| 2013/0186302 A1 | 7/2013 | Naidoo et al. | |
| 2013/0239850 A1 | 9/2013 | Naidoo et al. | |
| 2013/0295394 A1 | 11/2013 | Hong et al. | |
| 2014/0000479 A1 | 1/2014 | Stevens et al. | |
| 2014/0033951 A1 | 2/2014 | Ech et al. | |
| 2014/0261076 A1 | 9/2014 | Quinn et al. | |
| 2015/0225358 A1 | 8/2015 | Howard et al. | |
| 2016/0297969 A1 | 10/2016 | Naidoo et al. | |
| 2017/0283615 A1 | 10/2017 | Williams et al. | |

FOREIGN PATENT DOCUMENTS

| | | |
|---|---|---|
| CN | 101696097 A | 4/2010 |
| CN | 102092988 A | 6/2011 |
| CN | 102443271 A | 5/2012 |
| CN | 102702760 A | 10/2012 |
| CN | 102786806 A | 11/2012 |
| CN | 102838317 A | 12/2012 |
| CN | 102838874 A | 12/2012 |
| CN | 102964858 A | 3/2013 |
| CN | 102977620 A | 3/2013 |
| CN | 103102703 A | 5/2013 |
| CN | 103497521 A | 1/2014 |
| CN | 103602087 A | 2/2014 |
| CN | 103709415 A | 4/2014 |
| CN | 103788665 A | 5/2014 |
| CN | 103788667 A | 5/2014 |
| CN | 103980147 A | 8/2014 |
| CN | 104250520 A | 12/2014 |
| DE | 19519539 A1 | 12/1995 |
| DE | 195 01 212 A1 | 6/1996 |
| DE | 196 01 495 A1 | 7/1997 |
| EP | 0568757 A1 | 11/1993 |
| EP | 0999237 A1 | 5/2000 |
| EP | 1524300 A1 | 4/2005 |
| EP | 1696002 A1 | 8/2006 |
| EP | 1717275 A1 | 11/2006 |
| EP | 2083050 A1 | 7/2009 |
| EP | 2245090 A1 | 11/2010 |
| FR | 2963354 A1 | 7/2010 |
| GB | 584344 | 1/1947 |
| GB | 610629 | 10/1948 |
| JP | 3158251 B2 | 7/2000 |
| JP | 2012046641 A | 3/2012 |
| JP | 5341892 B2 | 11/2012 |
| KR | 101166155 B1 | 7/2012 |
| KR | 101487180 B1 | 1/2015 |
| RU | 2461594 C1 | 9/2012 |
| WO | 93/00406 A1 | 1/1993 |
| WO | 97/35940 A1 | 10/1997 |
| WO | 00/20537 A1 | 4/2000 |
| WO | 2006/107179 A2 | 10/2006 |
| WO | 2007/062158 A2 | 5/2007 |
| WO | 2009/102877 A1 | 8/2009 |
| WO | 2016/033605 A1 | 3/2016 |

OTHER PUBLICATIONS

International Search Report and Written Opinion for corresponding Application No. PCT/US2015/047810 (dated Dec. 3, 2015).
Podolsky et al., "Comparative Performance of Bio-Derived/Chemical Additives in Warm Mix Asphalt at Low Temperature," 51st Annual Petersen Asphalt Research Conference, Iowa State University (Jul. 16, 2014).
Office Action for U.S. Appl. No. 15/445,307 dated (Jan. 11, 2019).
Office Action for U.S. Appl. No. 15/691,295 dated (Apr. 4, 2019).
Material Safety Data Sheet for Epoxidized Isoamyl Soyate, Revision Date: Feb. 5, 2010.
Material Safety Data Sheet for Glycerin Removal Column Bottoms, Revision Date: Feb. 29, 2012.
Material Safety Data Sheet for MONG, Revision Date: Oct. 11, 2012.
Material Safety Data Sheet for Mixed Short Chain Polyols, Revision Date: Mar. 25, 2011.
Material Safety Data Sheet for ADM CA118, Revision Date: Jun. 25, 2014.
Material Safety Data Sheet for Alinco Z-2 Z-3 Linseed Oil, Revision Date: Feb. 12, 2014.
Material Safety Data Sheet for OKO M-37 Linseed Oil, Issue Date: Jul. 10, 2002.
Material Safety Data Sheet for Toplin X-Z Linseed Oil, Issue Date: Aug. 18, 2005.
Elkashef et al., "Instroducing a Soybean Oil-Derived Material as a Potential Rejuvenator of Asphalt Through Rheology, Mix Characterisation and Fourier Transform Infrared Analysis," Road Materials and Pavement Design 19(8):1750-1771 (2018).
Elkashef et al., "Preliminary Examination of Soybean Oil Derived Material as a Potential Rejuvenator Through Superpave Criteria and Asphalt Bitumen Rheology," Construction and Building Materials 149:826-836 (2017).
Elkashef et al., "Improving Fatigue and Low Temperature Performance of 100% RAP Mixtures Using a Soybean-Derived Rejuvenator," Construction and Building Materials 151:345-352 (2017).

* cited by examiner

ASPHALT PRODUCTS AND MATERIALS AND METHODS OF PRODUCING THEM

This application is a national stage application under 35 U.S.C. § 371 of PCT Application No. PCT/US2015/047810, filed Aug. 31, 2015, which claims the benefit of U.S. Provisional Patent Application Ser. Nos. 62/044,028, filed Aug. 29, 2014, and 62/046,105, filed Sep. 4, 2014, which are hereby incorporated by reference in their entirety.

FIELD OF THE INVENTION

The present invention relates to improved asphalt products and materials and methods of producing them.

BACKGROUND OF THE INVENTION

Asphalt or flexible pavement is typically built with several layers to form a layered system with better materials at the top where the stress intensity is high and inferior materials at the bottom where the stress intensity is low. The top layer, called the surface course, is typically made of an asphalt mixture. All types of failure or distress can be classified by whether they are structural or functional failures and load associated or non-load associated distresses. Surface course aging is considered a non-load associated distress caused by climate/environmental effects. Many environmental factors can cause surface course aging damage, such as ozone, UV rays, oxygen, and thermal radiation. Oxidative aging causes the asphalt binder to become harder and more brittle.

Most of the short-term aging that occurs in asphalt begins with the blending of the aggregate with asphalt binders. The blending temperature in the asphalt plant primarily controls the oxidative aging rate of the asphalt. The short-term aging for the asphalt binder in the mixture continues until the end of the pavement construction. Methods such as warm mix asphalt and cold mix asphalt are the main solutions to reduce the short-term aging via heating and constructing the asphalt mixture at lower temperatures compared with hot mix asphalt.

During the service life, the long-term oxidative aging begins and occurs at a much slower rate than the rate of aging during mixing and construction. The brittleness of the asphalt mixture gradually increases due to physico-chemical changes in the binder. Exudation, evaporation, oxidation, and physical aging are all related to asphalt binder aging, while oxidation and physical hardening (steric hardening) are the most important direct consequences. Physical aging is a reversible process, which can produce changes in rheological, electrical, and caloric properties, etc., without altering the chemical composition of the material. The oxidation of asphalt binder caused by chemical reactions causes transformations in the asphalt components. Asphalt oxidation is the main cause of long-term deterioration and eventually results in cracking in asphalt pavements. The asphalt can be separated into four generic fractions namely: asphaltenes, polar aromatics, naphthene aromatics, and saturates. Each fraction provides different properties. Asphaltenes mainly contribute to the viscosity (hardening effect), and the aromatics and saturates are correlated to the ductility (elastic effect). Many researchers have compared the fractions of aged asphalt with fractions of unaged asphalt. It was found that the oxidation of asphalt had an effect on chemical properties and, consequently, on the rheological properties. While asphalt is aging, the viscosity increases due to the oxidative conversion of polar aromatics to asphaltenes. This transformation between the components during oxidation can be described as follows: Aromatics→Resins→Asphaltenes. The polymerization or condensation of the asphaltenes create larger molecules with long chained structures which harden the asphalt. The oxidation causes a great increase in the asphaltenes, including those with high molecular weight. This asphalt hardening theory can be used to explain a condition known as the air-blown asphalt phenomena. An antioxidant is added to stop or delay the oxidative processes that convert aromatic fractions.

Historically, growth of bio-based chemical products in the world market has typically been limited due to their higher production costs compared to crude petroleum derived products. However due to the variability of crude petroleum pricing, increasing demand for environmentally friendly products from a growing population and limited amount of nonrenewable resources, growth for bio-based chemical products has increased. This market growth has propelled the number and size of bio-refineries to increase in the past ten years. Depending on the production process, bio-refineries can produce a sizable amount of material with surfactant characteristics. These materials are candidates for use as bio-based warm mix asphalt (WMA) additive technologies.

The present invention is directed to overcoming these and other deficiencies in the art.

SUMMARY OF THE INVENTION

One aspect of the present invention relates to a method of producing an improved asphalt. The method involves providing an asphalt and providing a compound of formula (I)

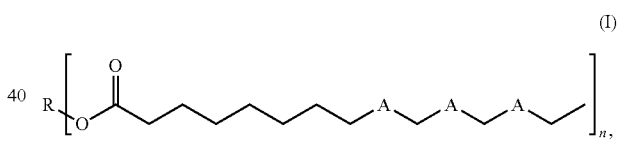

wherein:

each A is selected independently at each occurrence thereof from the group consisting of

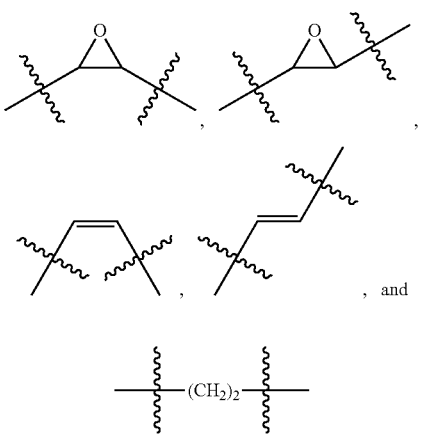

and
wherein at least one A is

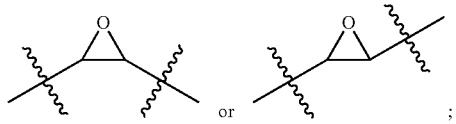 [SMILES: *C1OC1* ; *C1OC1*]

each

represents the point of attachment to a —CH$_2$— group;
n is 1, 2, or 3;
R is selected from the group consisting of H, C$_1$-C$_{23}$ alkyl, and benzyl, wherein the C$_1$-C$_{23}$ alkyl can be optionally substituted with an aryl, heteroaryl, or heterocyclyl; or
R is selected from the group consisting of

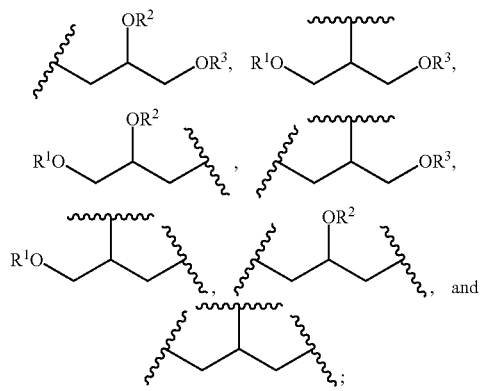

each

represents the point of attachment to a

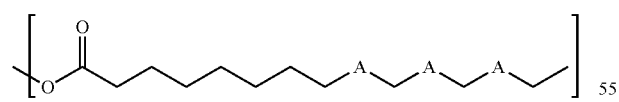

moiety;
R$^1$, R$^2$, and R$^3$ are independently selected from the group consisting of —H and —C(O)R$^4$;
R$^4$ is H, C$_1$-C$_{23}$ alkyl, or aryl. The asphalt is mixed with the compound of formula (I) under conditions effective to produce an improved asphalt.

Another aspect of the present invention relates to a method of producing an improved polymer modified asphalt. The method involves providing a polymer modified asphalt and providing a compound of formula (IIa) or formula (IIb)

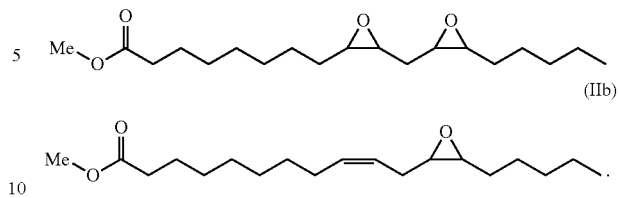

The polymer modified asphalt is mixed with the compound of formula (IIa) or formula (IIb) under conditions effective to produce an improved polymer modified asphalt.

Another aspect of the invention relates to an asphalt product. The asphalt product includes an asphalt and a compound of formula (I)

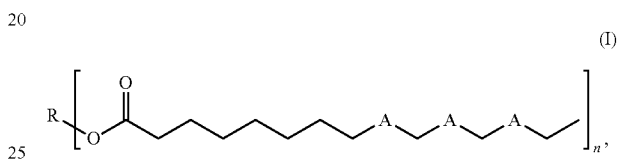

wherein:
each A is selected independently at each occurrence thereof from the group consisting of

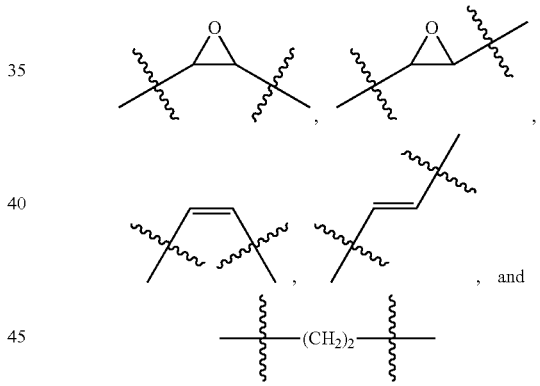

and
wherein at least one A is

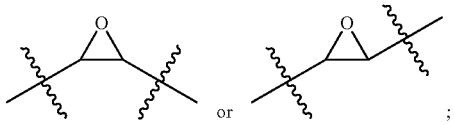 [SMILES: *C1OC1* ; *C1OC1*]

each

represents the point of attachment to a —CH₂— group;

n is 1, 2, or 3;

R is selected from the group consisting of H, $C_1$-$C_{23}$ alkyl, and benzyl, wherein the $C_1$-$C_{23}$ alkyl can be optionally substituted with an aryl, heteroaryl, or heterocyclyl; or R is selected from the group consisting of

[structures showing OR², OR³, R¹O substituted groups]

each

[structure]

represents the point of attachment to a

[structure showing the moiety with A-A-A chain and ester group]

moiety;

R¹, R², and R³ are independently selected from the group consisting of —H and —C(O)R⁴;

R⁴ is H, $C_1$-$C_{23}$ alkyl, or aryl, mixed with the asphalt.

Another aspect of the invention relates to a polymer modified asphalt product. The asphalt product includes a polymer modified asphalt and a compound of formula (IIa) or (IIb)

(IIa)

[structure: Me-O-C(=O)-(CH₂)₆-epoxide-epoxide-alkyl]

(IIb)

[structure: Me-O-C(=O)-(CH₂)₆-CH=CH-epoxide-alkyl]

mixed with the polymer modified asphalt.

A further aspect of the present invention relates to a method of making an asphalt material. The method includes providing an improved asphalt product comprising an asphalt and a compound of formula (I)

(I)

$$R\left[O-C(=O)-(CH_2)_n-A-A-A-\right]_n,$$

wherein:

each A is selected independently at each occurrence thereof from the group consisting of

[epoxide structures, alkene structures (cis and trans), and —(CH₂)₂— ]

, and and wherein at least one A is

[two epoxide structures]

or

;

each

[structure]

represents the point of attachment to a —CH₂— group;

n is 1, 2, or 3;

R is selected from the group consisting of H, $C_1$-$C_{23}$ alkyl, and benzyl, wherein the $C_1$-$C_{23}$ alkyl can be optionally substituted with an aryl, heteroaryl, or heterocyclyl; or R is selected from the group consisting of

[structures showing OR², OR³, R¹O substituted groups]

, and

-continued

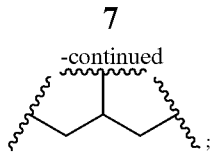

each

represents the point of attachment to

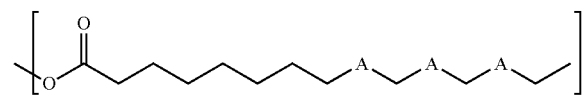

moiety;

$R^1$, $R^2$, and $R^3$ are independently selected from the group consisting of —H and —C(O)R$^4$;

$R^4$ is H, $C_1$-$C_{23}$ alkyl, or aryl, mixed with the asphalt. The method further includes mixing the improved asphalt product with a mineral aggregate at a temperature of 150° C. or lower, to coat the mineral aggregate and produce a heated paving material which, at a warm mix temperature, has a compaction production temperature at least 15-50° C. lower than that produced when the improved asphalt material is prepared in the absence of the compound of formula (I). The heated paving material is applied to a surface to be paved to form an applied paving material. The applied paving material is compacted to a void fraction of less than 8%, at a compacting temperature of 140° C. or lower to form a paved surface.

Epoxidized fatty acid ester compounds have shown potential as warm mix asphalt (WMA) additives in preliminary laboratory testing. WMA additives reduce the mixing and compaction temperature of Hot Mix Asphalt (HMA) by approximately 30° F. to 100° F. The benefits of WMA additives include reduced emissions, savings in fuel costs associated with reduced plant temperatures, construction benefits such as longer haul distances, cooler weather paving, and reduced compaction effort.

Epoxidized fatty acid esters are WMA additives that improve low temperature binder performance of asphalt. For asphalt pavements, both short and long term aging can cause deterioration and eventually result in cracking, rutting, and stripping. The present invention relates to WMAs including epoxidized fatty acid esters for utilization as an additive in asphalt. Using these esters in asphalt production represents an economical alternative to conventional methods while being conscious of the environment, improving worker safety, lowering compaction temperatures, improving mix compactibility, reducing asphalt binder viscosity, and increasing the longevity and performance of asphalt pavements. As a pavement ages, it becomes stiffer and more susceptible to failure. The use of WMAs as an asphalt additive is an attractive way to increase the longevity and enhance the performance of asphalt pavements.

For laboratory testing, an unmodified Montana crude source supplied by Jebro, with a performance grade ("PG") of 58-28 was used as a first binder along with a polymer modified form of this binder as a second binder—the PG 58-28 binder polymer modified with 1.5% styrene-butadiene-styrene (SBS) to achieve a PG 64-28 binder. The WMA additives tested were various epoxidized fatty acid esters, including epoxidized methyl soyate, epoxidized benzyl soyate, epoxidized soybean oil, epoxidized isoamyl soyate, and epoxidized corn oil. The dosage levels chosen were 0.5%, and/or 0.75% for addition of each epoxidized fatty acid ester. Binder testing included specific gravity, dynamic shear rheometer (DSR) testing on original and aged binders as well as bending beam rheometer tests. Aging included both rolling thin film oven (RTFO) and pressure aging vessel (PAV) aging which simulate short and long term aging of the asphalt, respectively. Mass loss of the binder was measured after RTFO testing. All binder testing followed American Association of State Highway and Transportation Officials (AASHTO) protocols. Asphalt mix testing included moisture sensitivity testing and rutting at high temperature using the Hamburg Wheel Tracking test, and low temperature testing was done by using the Semi-circular Bend test to determine the resistance to cracking/fatigue.

WMA is asphalt concrete that is mixed and compacted at substantially lower temperatures that those used to produce hot mix asphalt (HMA). WMA technologies are known best for their ability to reduce asphalt binder viscosity, and decrease mixing and compaction temperatures for asphalt mixtures. With WMA use mixing and compaction temperatures can be decreased by as much as 20° C. to 55° C. A temperature decrease makes it possible to save on cost because fuel usage is lowered. An additional benefit is that emissions of greenhouse gases (GHG) are reduced as well, thus improving air quality and lowering the exposure of workers to fumes. Lower compaction temperatures and improved mix compactibility are achieved, with reduced asphalt binder viscosity. Because of lower compaction temperatures, contractors can extend their paving season in colder climates. Increased use of reclaimed asphalt pavement in WMA mixtures is also possible because the asphalt binder viscosity is reduced. Button et al., "A Synthesis of Warm Mix Asphalt," Rep No FHWA/TX-07/0-5597-1, College Station, Tex.: Texas Transportation Institute (2007); D'Angelo et al., "Warm-Mix Asphalt: European Practice," Publication FHWA-PL-08-007: FHWA, U.S. Dept. of Transportation, Washington, D.C. (2008); Gandhi T., "Effects of Warm Asphalt Additives on Asphalt Binder and Mixture Properties: Ph.D. dissertation," Clemson Univ., Clemson, S.C. (2008); Hassan M., "Life-Cycle Assessment of Warm-Mix Asphalt: An Environmental and Economic Perspective," Transportation Research Board 88th Annual Meeting, Washington, D.C. (2009); Hurley et al., "Evaluation of Evotherm for Use in Warm Mix Asphalt," Rep No 06-02. Auburn, Ala.: National Center for Asphalt Technology (2006); Jenkins et al., "Half-Warm Foamed Bitumen Treatment, a New Process," 7th Conference on Asphalt Pavements for Southern Africa (CAPSA 99) (1999); Kristjánsdóttir Ó., "Warm-Mix Asphalt for Cold Weather Paving," Seattle, Wash.: Univ. of Washington (2006); Kristjánsdóttir et al., "Assessing Potential for Warm-Mix Asphalt Technology Adoption," *Transp Res Rec.* 2040:91-9 (2007); Larsen et al., "WAM Foam Asphalt Production at Lower Operating Temperatures as an Environmental Friendly Alternative to HMA," 3rd Eurasphalt & Eurobitume Congress: Foundation Eurasphalt, Breukelen, Netherlands (2004); Perkins S. W., "Synthesis of Warm Mix Asphalt Paving Strategies for use in Montana Highway Construction," Rep No FHWA/MT-09-009/8117-38. Helena, Mont.: Western Transportation Institute (2009); Prowell et al., "Field Performance of Warm-Mix Asphalt at the NCAT Test Track," Transportation Research Board 86th Annual Meeting: Washington, D.C. (2007); and Kim et al., "Influence of Warm Mix Additives on PMA Mixture Properties," *Journal of Transportation Engineering* 138(8):991-7 (2012), all of which are hereby incorporated by reference in their entirety.

There are four categorized groups of WMA technologies: (i) foaming—water based; (2) foaming—water bearing additive; (3) chemical additive; and (4) organic/bio-derived additives. It is hypothesized that softening could be occurring at high temperatures decreasing the resistance to rutting and stripping for the warm mix asphalt (WMA) mixtures modified with bio-derived/chemical additives as compared to a hot mix control.

These epoxidized fatty acid ester additives help to decrease emissions produced during HMA production. This allows the asphalt industry the opportunity to reduce their carbon footprint, save money associated with increased plant temperatures and lessen fumes workers are exposed to during production and construction. D'Angelo et al., "Warm-Mix Asphalt: European Practice," Publication FHWA-PL-08-007: FHWA, U.S. Dept. of Transportation, Washington, D.C. (2008), which is hereby incorporated by reference in its entirety. Reducing asphalt plant temperatures helps protect plant equipment from wear and tear. These combined benefits help to make asphalt a more sustainable product for the environment, the contractor, and the general public.

As the cost of crude petroleum and asphalt prices continue to trend upward, saving money by using WMA additives becomes increasingly important for maintaining a competitive edge in the market. As base material costs increase, WMA can help contractors save money because of the reduced fuel costs and higher percentages of recycled asphalt pavement that can be incorporated in WMA mixes. In addition to savings, WMA has been shown to produce a quality asphalt product. In many field produced mixes, there has been no performance difference between the WMA and control pavement sections. Laboratory tests have shown concern regarding moisture susceptibility in WMA. This is likely due to incomplete drying of aggregates. Hurley et al., "Evaluation of Evotherm for Use in Warm Mix Asphalt," Rep No 06-02. Auburn, Ala.: National Center for Asphalt Technology (2006), which is hereby incorporated by reference in its entirety. Overall, WMA has shown promise and is quickly being implemented by owner-agencies around the country.

DETAILED DESCRIPTION OF THE INVENTION

One aspect of the present invention relates to a method of producing an improved asphalt. The method involves providing an asphalt and providing a compound of formula (I)

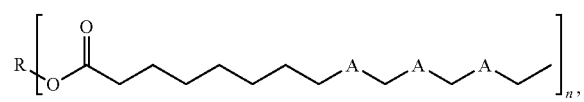

(I)

wherein:
each A is selected independently at each occurrence thereof from the group consisting of

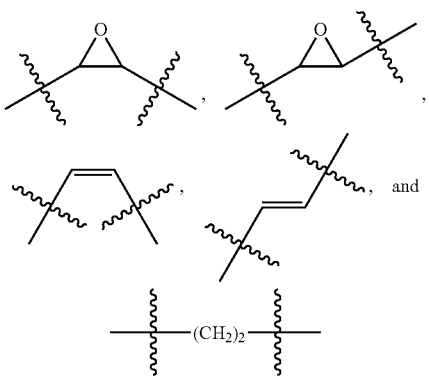

and
wherein at least one A is

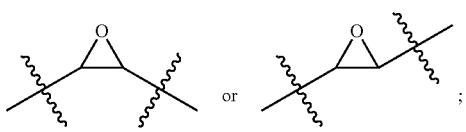 [SMILES: *C1OC1* ; *C1OC1*]

each

represents the point of attachment to a —CH$_2$— group;
n is 1, 2, or 3;
R is selected from the group consisting of H, C$_1$-C$_{23}$ alkyl, and benzyl, wherein the C$_1$-C$_{23}$ alkyl can be optionally substituted with an aryl, heteroaryl, or heterocyclyl; or
R is selected from the group consisting of

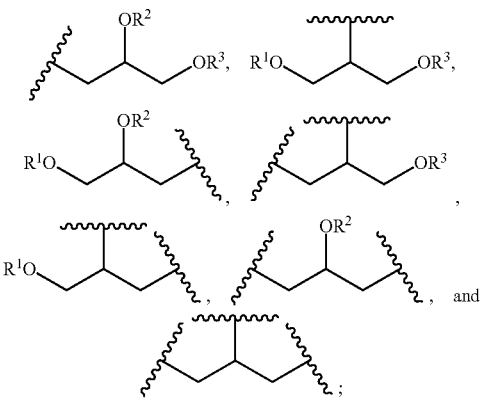

each

represents the point of attachment to a

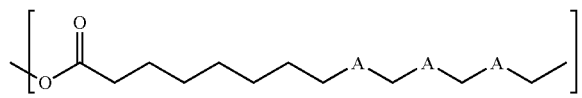

moiety;

$R^1$, $R^2$, and $R^3$ are independently selected from the group consisting of —H and —C(O)$R^4$;

$R^4$ is H, $C_1$-$C_{23}$ alkyl, or aryl. The asphalt is mixed with the compound of formula (I) under conditions effective to produce an improved asphalt.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 23 carbon atoms in the chain. For example, straight or branched carbon chain could have 1 to 10 carbon atoms. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "benzyl" means a benzyl group as shown below

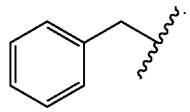

The term "aryl" means an aromatic monocyclic or multicyclic ring system of 6 to about 14 carbon atoms, preferably of 6 to about 10 carbon atoms. Representative aryl groups include phenyl and naphthyl.

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxopyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, oxiranyl, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "epoxide" or "oxirane" includes an epoxide ring (i.e., group) as shown below:

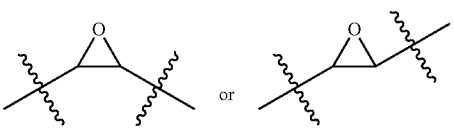

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture.

Compounds described herein may contain one or more epoxide (oxirane) rings, and unless specified otherwise, it is intended that the compounds include both cis- or trans-isomers and mixtures thereof. When the compounds described herein contain olefinic double bonds or other centers of geometric asymmetry, and unless specified otherwise, it is intended that the compounds include both E and Z geometric isomers.

Asphalt includes material in which the predominating constituents are bitumens, which occur in nature or are obtained in petroleum processing. Bitumens include solid, semisolid, or viscous substances, natural or manufactured, composed principally of high molecular weight hydrocarbons. The asphalt used in the present invention is not particularly limited, and various kinds of asphalts may be used in the present invention. Examples of the asphalt include straight asphalts such as petroleum asphalts for pavements, as well as polymer-modified asphalts produced by modifying asphalt with a polymer material including a thermoplastic elastomer such as styrene/butadiene block copolymers (SBS), styrene/isoprene block copolymers (SIS), and ethylene/vinyl acetate copolymers (EVA).

Suitable grades of asphalt include, but are not limited to, the following: PG52-22, PG58-22, PG64-22, PG67-22, PG70-22, PG76-22, PG82-22, PG52-28, PG58-28, PG64-28, PG67-28, PG70-28, PG76-28, PG52-34, PG58-34, PG64-34, PG64-16, PG67-16, PG70-16, PG76-16, PG64-10, PG67-10, PG70-10, PG76-10, pen grade 40-50, pen grade 60-70, pen grade 85-100, pen grade 120-150, AR4000, AR8000, AC10 grade, AC20 grade, and AC30 grade. Roberts et al., "Hot Mix Asphalt Materials, Mixture Design, and Construction," *NAPA Research and Education Foundation* (2nd ed.) (1996), which is hereby incorporated by reference in its entirety.

Renewable source-derived fats and oils comprise glycerol triesters of fatty acids. These are commonly referred to as "triglycerides" or "triacylglycerols ("TAG")." Fats and oils are usually denoted by their biological source and contain several different fatty acids typical for each source. For example, the predominant fatty acids of soybean oil are the unsaturated fatty acids oleic acid, linoleic acid, and linolenic acid, and the saturated fatty acids palmitic acid and stearic acid. Other fatty acids are present at low levels. Triglycerides are the main component of natural oils and are composed of three fatty acids groups connected by a glycerol centre. Epoxidized triglycerides can be found as such in nature, for instance in *Vernonia* plants, or can be conveniently synthesized from more common unsaturated oils by using a standard epoxidation process. See U.S. Patent Publ. No. 20120156484 to Vendamme et al., which is hereby incorporated by reference in its entirety.

Unsaturated fatty acids are susceptible to epoxidation to form fatty acids bearing epoxide rings. Thus, triglycerides containing unsaturated fatty acids can be subjected to epoxidation to form epoxidized triglycerides in which one, two, or all three fatty acids bear at least one epoxide ring. Diglycerides (diacylglycerols, "DAG") are obtained when one fatty acid is removed from a triglyceride, typically by hydrolysis; monoglycerides (monoacylglycerols, "MAG") are obtained when two fatty acids are removed from a triglyceride.

Epoxidized fatty acid ester according to the present invention means that at least one of the double bonds of the unsaturated fatty acid ester is oxidized to an epoxy group. Such oxidations are well known in the art and can be readily accomplished in an industrial scale, e.g., by using hydrogen peroxide and a carboxylic acid (e.g., formate or acetate), or by the halohydrin method. It is understood by those skilled in the art that in practice, epoxidized fatty acid esters may contain various quantities of by-products arising from hydrolysis or rearrangement of epoxides and from cross-linking of the fatty acid chains. Use of epoxidized fatty acid esters containing small quantities of epoxidation by-products and epoxide decomposition by-products is included within the scope of the present disclosure. WO 2007062158 to Selifonov, which is hereby incorporated by reference in its entirety.

Epoxidized fatty acids can be subjected to esterification reactions with polyhydric alcohols (such as sugars, sugar acids, glycerol and glycols) to form epoxidized esters of polyols, or with monohydric alcohols (such as benzyl alcohol, methanol, ethanol, propanols, butanols and longer alcohols, furan-containing alcohols (such as tetrahydro-2-furanmethanol and 2-furanmethanol), glycidol, and fusel oil) to form epoxidized monoesters. Alternatively, epoxidized esters of polyols or of monohydric alcohols can be obtained by subjecting the esters to epoxidation.

In addition, triglyceride oils have long been subjected to a process called "blowing" to make blown oils. In this process, the triglycerides are heated in the presence of air or oxygen (often blown through the oil). The double bonds of the fatty acids in the oils react to form both epoxides and dimers of the oils. The epoxidized crosslinked oil can be subjected to hydrogenation (a common vegetable oil process for removing double bonds from oils) to yield asphalt modifiers. Useful processes are described in U.S. Pat. Nos. 7,994,107, 8,198,223, and 8,198,224 to Bloom, all of which are hereby incorporated by reference in their entirety.

Renewable source derived fats and oils include algal oil, animal fat, beef tallow, borneo tallow, butterfat, camelina oil, candlefish oil, canola oil, castor oil, cocoa butter, cocoa butter substitutes, coconut oil, cod-liver oil, colza oil, coriander oil, corn oil, cottonseed oil, false flax oil, flax oil, float grease from wastewater treatment facilities, hazelnut oil, hempseed oil, herring oil, illipe fat, jatropha oil, kokum butter, lanolin, lard, linseed oil, mango kernel oil, marine oil, meadowfoam oil, menhaden oil, microbial oil, milk fat, mowrah fat, mustard oil, mutton tallow, neat's foot oil, olive oil, orange roughy oil, palm oil, palm kernel oil, palm kernel olein, palm kernel stearin, palm olein, palm stearin, peanut oil, phulwara butter, pile herd oil, pork lard, radish oil, ramtil oil, rapeseed oil, rice bran oil, safflower oil, sal fat, salicornia oil, sardine oil, sasanqua oil, sesame oil, shea fat, shea butter, soybean oil, sunflower seed oil, tall oil, tallow, tigernut oil, tsubaki oil, tung oil, triacylglycerols, triolein, used cooking oil, vegetable oil, walnut oil, whale oil, white grease, yellow grease, and derivatives, conjugated derivatives, genetically-modified derivatives, and mixtures of any thereof.

The fatty acid esters of the present invention may be modified or unmodified, partially or fully epoxidized, or partially or fully hydrogenated. In one embodiment, the compound of formula (I) is methylated and/or hydrogenated. The fatty acid esters of the present invention may be derived from a plant oil, animal fat, or a synthetic triglyceride. In one embodiment, the compound of formula (I) is the compound of any one of formulae (Ia)-(Ik):

or isomers thereof.

The fatty acid esters derived from plant or animal oil of the present invention may be polymerized. The polymerized plant oil or animal oil can be subsequently partially or fully saturated via a catalytic hydrogenation post-polymerization. The monomeric oils used in the epoxidized fatty acid esters can be any triglycerides or triglyceride mixtures that are radically polymerizable. These triglycerides or triglyceride mixtures are typically plant oils. Suitable plant oils include, but are not limited to, a variety of vegetable oils such as soybean oil, peanut oil, walnut oil, palm oil, palm kernel oil, sesame oil, sunflower oil, safflower oil, rapeseed oil, linseed oil, flax seed oil, colza oil, coconut oil, corn oil, cottonseed

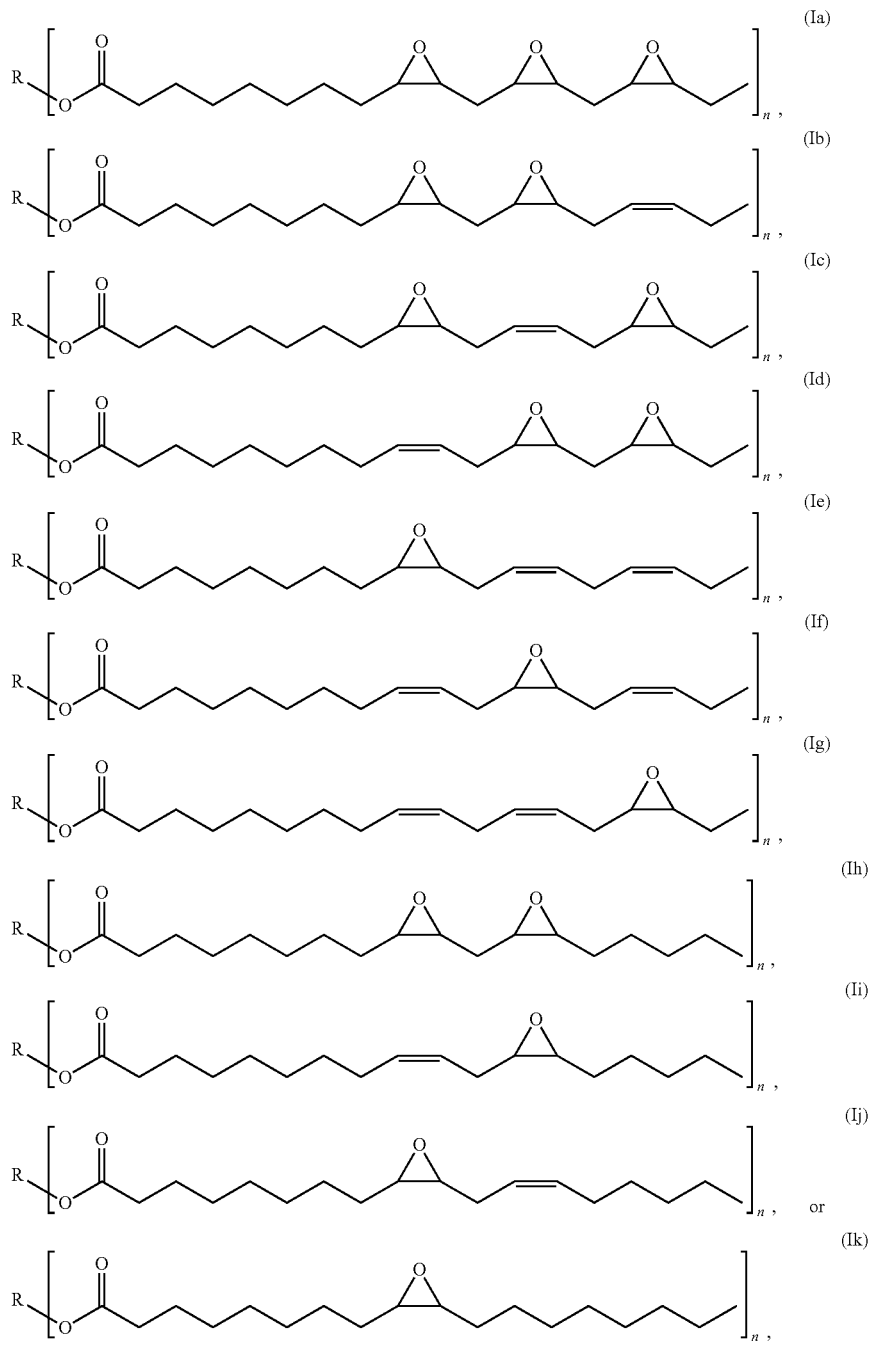

oil, olive oil, castor oil, false flax oil, hemp oil, mustard oil, radish oil, ramtil oil, rice bran oil, salicornia oil, tigernut oil, tung oil, etc., and mixtures thereof. Typical vegetable oil used herein includes soybean oil, linseed oil, corn oil, flax seed oil, or rapeseed oil, and the resulting epoxidized fatty acid ester is polymerized triglyceride or triglyceride derivatives.

Suitable epoxidized fatty acid esters according to the present invention include, but are not limited to, epoxidized methyl soyate, epoxidized benzyl soyate, epoxidized soybean oil, epoxidized isoamyl soyate, and epoxidized corn oil. The fatty acid esters may also include, for example, epoxidized methyl linoleate; benzyl, ethyl, fusel oil, furanoic alcohols (tetrahydro-2-furanmethanol and 2-furanmethanol), glycidol, SBO TAG, DAG, MAG, glycols, and blown oils such as the above-mentioned linseed oil, rapeseed oil, castor oil and soybean oil.

Epoxidized triglycerides are commercially available. See U.S. Patent Publ. No. 20120156484 to Vendamme et al., which is hereby incorporated by reference in its entirety. For example, epoxidized linseed oil (ELO) is available from Cognis (Düsseldorf, Germany) under the trade name DEHYSOL B316 SPEZIAL, or Arkema (King of Prussia, Pa.) under the trade name VIKOFLEX 7190. An exemplary structure of an epoxidized triglyceride of linseed oil is as follows:

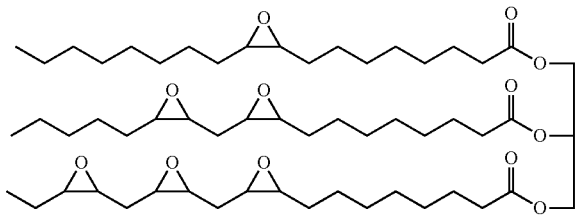 [SMILES: CCCCCCCCC1OC1CCCCCCCC(=O)OCC(COC(=O)CCCCCCCC1OC1CC1OC1CC1OC1CC)OC(=O)CCCCCCCC1OC1CC1OC1CCCCC]

Epoxidized soybean oil (ESBO) is commercially available from Cognis (Düsseldorf, Germany) under the trade name DEHYSOL D82, or from Arkema (King of Prussia, Pa.) under the trade name VIKOFLEX 7170. See U.S. Patent Publ. No. 20120156484 to Vendamme et al., which is hereby incorporated by reference in its entirety.

Methods of making epoxidized methyl soyate are known in the art. See U.S. Pat. No. 9,000,196 to Hagberg et al., and U.S. Pat. No. 6,797,753 to Benecke et al, both of which are hereby incorporated by reference in their entirety. Soyate relates to a mixture of fatty acids derived from soybean oil. "Methyl oleate" describes the methyl ester of only oleic acid, "methyl soyate" describes the product of the reaction of making methyl esters of soybean oil. Most biodiesel sold in the USA is just methyl soyate with a few additives.

Primary plasticizers have been reported where the plasticizers contain fatty acids derived from vegetable oils and the fatty acids are substantially fully esterified with an alcohol (monool or polyol), the fatty acids have unsaturated bonds that are substantially fully epoxidized, and the fatty acids are added substantially randomly to one or more hydroxyl sites on the alcohol. See U.S. Pat. No. 6,797,753 to Benecke et al, which is hereby incorporated by reference in its entirety. Primary plasticizers include, but are not limited to, epoxidized pentaerythritol tetrasoyate, epoxidized propylene glycol disoyate, epoxidized ethylene glycol disoyate, epoxidized methyl soyate, epoxidized sucrose octasoyate, and the epoxidized product of soybean oil interesterified with linseed oil.

There are several known methods by which these plasticizers may be made. See U.S. Pat. No. 6,797,753 to Benecke et al, which is hereby incorporated by reference in its entirety. In one embodiment, the vegetable oil fatty acids are linked by direct esterification to monoalcohols or polyalcohols, and the esterified products are then epoxidized. In an additional embodiment, the direct esterification step is replaced with transesterification, whereby the monool or polyol reacts with a lower alkyl ester of a vegetable oil fatty acid to produce the desired ester plus a lower alcohol. The ester is then epoxidized. In yet another embodiment, a first ester is interesterified with a second ester, and the desired ester is again epoxidized.

Epoxidized fatty acid esters useful as primary plasticizers in a phthalate-free system and which are suitably nonvolatile, not petroleum-based, and capable of imparting thermal stability to formulations presently using phthalate plasticizers, including those based on PVC, other halogenated polymers, acid-functionalized polymers, anhydride-functionalized polymers, and nitrile rubbers are known in the art and described in WO 2009/102877 to Eaton, which is hereby incorporated by reference in its entirety.

Suitable epoxidized fatty acid ester plasticizers may include epoxidized biodiesel (conventionally, fatty acid methyl esters of soy, rapeseed or palm oils, though $C_1$-$C_{14}$ esters are more generally contemplated) and epoxidized derivatives of fatty acid esters of biodiesel. Methods for making the epoxidized fatty acid esters involve formation of the fatty acid ester first, followed by epoxidation of the ester.

Epoxidized methyl soyate esters are known to those skilled in the art to be made starting from epoxidized soybean oil by alcoholysis, see U.S. Pat. No. 3,070,608 to Kuester et al., which is hereby incorporated by reference in its entirety. For example, epoxidized soybean oil may be reacted with a molar excess of methanol in the presence of sodium methoxide as a catalyst, to produce epoxidized methyl soyate. The total epoxide content in going from epoxidized soybean oil to epoxidized methyl soyate, as being relatively unchanged showing "little or no decrease".

Reduced color epoxidized fatty acid esters (such as epoxidized methyl soyate) according to the present invention can be made from an epoxidized natural fat or oil (such as epoxidized soybean oil) through the inclusion of borohydride in either a transesterification process or in an interesterification process. See U.S. Patent Publ. No. 2014/0113999 to Howard et al., which is hereby incorporated by reference in its entirety.

In accordance with the present invention, the addition of the borohydride and starting from an epoxidized natural fat or oil does not to detract in a material way from the other commercially-relevant performance attributes of a plasticized polymer composition incorporating such a reduced color epoxidized fatty acid ester, as compared to an equivalent composition prepared using an epoxidized fatty acid ester made according to the methods known in the art. Given the indication in the WO 2009/102877 to Eaton, which is hereby incorporated by reference in its entirety, that epoxides made from esters of fatty acids such as the epoxidized methyl ester of soy oil are often too volatile to serve as useful plasticizers of PVC, this was a finding of considerable significance for the specific reduced color epoxidized fatty acid ester, epoxidized methyl soyate or EMS. Rather than being dependent on the production economics or availability of biodiesel, which are in turn to some extent dependent on fuels demand, pricing and usage patterns, epoxidized methyl soyate esters could be made with an available supply of epoxidized soybean oil—the supply and demand for which is at least to some extent related to demand for the same plasticized PVC compositions in which ESO can be used as a secondary plasticizer and thermal stabilizer, and not to conditions in the fuel markets.

Alternatively, epoxidized fatty acid esters (especially of benzyl alcohol) of the present invention can be made from fats or oils by the process of transesterifying a low moisture epoxidized natural fat or oil by combination with a first alcohol in the presence of a transesterification catalyst and under conditions which are effective for carrying out the transesterification reaction. After the resultant product mixture from the reaction of the first alcohol and low moisture epoxidized natural fat or oil phase separates into an epoxidized fatty acid ester phase and a second phase comprising byproduct glycerol, the second phase is substantially removed. The epoxidized fatty acid esters in the epoxidized fatty acid ester phase from the first transesterification step are combined with more of the first alcohol and with a second alcohol which includes 5 to 7 members in a ring structure in the presence of a transesterification catalyst and under conditions effective for forming epoxidized fatty acid esters of the second alcohol in a second transesterification step. The first alcohol is continuously removed during the second transesterification step. See U.S. Patent Publ. No. 2015/0225358 to Howard et al., which is hereby incorporated by reference in its entirety. Sodium borohydride may also be incorporated into the process to make lighter materials, if necessary.

Epoxidized fatty acid esters of the present invention, particularly benzyl esters, may be in the form of a composition comprising one or more unsaturated fatty acid esters of alcohols which include a five to seven member ring structure. That composition contains not more than about 5.0 percent by weight of the total weight of material of monoglycerides and diglycerides combined and can be made by the process disclosed in U.S. Pat. No. 8,703,849 to Hagberg et al., which is hereby incorporated by reference in its entirety.

The asphalt of the present invention may contain anywhere from 1% to 100% by weight epoxidized fatty acid ester. More preferably, the asphalt contains from about 3% to about 40% by weight epoxidized fatty acid ester. For example, the asphalt may contain about 1%, 2%, 3%, 4%, 5%, 6%, 7%, 8%, 9%, 25%, 40%, 50%, 60%, 70%, 80%, 90, or 100% by weight epoxidized fatty acid ester. In one embodiment, the epoxidized fatty acid ester is mixed in an amount of 0.1 to 5.0 wt. % with the asphalt. In various embodiments, the present invention includes a product produced by the methods described herein.

In the present invention, the term asphalt product includes a warm-melt flowable mixture of warm-mix binder of bituminous type optionally together with mineral filler. An asphalt product does not need to be roller compacted when implemented. It should thus be easily cast and spread. Examples of asphalt products include, in particular, asphalts, sealants, pavement seals and heat sealing materials.

The improved asphalt may optionally include a polymer additive, such as polyethylenes, oxidized polyethylenes, polyolefins, PE homopolymers, and the like. The polymer additive can include low molecular weight polymers, such as low, medium, or high density polyethylenes having a maximum viscosity of 1000 cps at 140° C. Other suitable polymers would include ethylenes and polypropylenes with melting points below 140° C. The polymer additive is preferably added at a concentration of up to about 1%, 5%, 10%, 15%, 20%, 25%, and 50% by weight of the improved asphalt.

The asphalt binder can be polymer-modified asphalt, preferably a styrene-butadiene type polymer-modified asphalt. Styrene-butadiene type polymers preferably include SB rubber, SBS linear type, SBS radial type, and SB sulphur linked type polymers, and the like. The asphalt binder optionally includes up to about 5% by weight styrene-butadiene type polymer. Any suitable polymer or mixture of different polymers can be used in producing polymer-modified asphalt. Non-limiting examples of suitable polymers include polyethylene, polypropylene, styrene/butadiene/styrene triblock copolymer, styrene/ethylene-butylene/styrene triblock copolymer, epoxy modified acrylate copolymer, ethylene/vinyl acetate copolymer, or mixture thereof.

The asphalt of the present aspect may have a viscosity of between 0.01 and 0.5 Pa·s at a temperature ranging from 130° C. to 165° C. For example, the viscosity at a temperature ranging from 130° C. to 165° C. may be 0.01 Pa·s, up to 0.05 Pa·s, between 0.01 and 0.1 Pa·s; between 0.01 and 0.2 Pa·s; between 0.01 and 0.3 Pa·s; between 0.01 and 0.4 Pa·s; and between 0.01 and 0.5 Pa·s. The temperature may be, for example, 130° C., between 130° C. and 140° C., between 130° C. and 150° C., between 130° C. and 160° C., or between 130° C. and 165° C. In one embodiment, the asphalt has a viscosity of 0.23-0.33 Pa·s at a temperature ranging from 130° C. to 150° C. In another embodiment, the asphalt has a viscosity of 0.13-0.21 Pa·s at a temperature ranging from 150° C. to 165° C.

According to the present invention, the improved asphalt may have a minimum compaction force index of 600 at a temperature ranging from 100° C. to 140° C. The asphalt may have a maximum compaction force index of 1650 at a temperature ranging from 100° C. to 140° C. In one embodiment, the improved asphalt may have a compaction force index of 818.7 to 1241.7 at a temperature ranging from 100° C. to 140° C. In another embodiment, the improved asphalt may have a compaction force index of 258 to 1559 at a temperature ranging from 100° C. to 140° C. Compaction energy may be evaluated through use of a Pine AFG2 gyratory compactor and may include moment, height, pressure, and angle of gyration. Abed, A. H., "Enhanced Aggregate-Asphalt Adhesion and Stability of Local Hot Mix Asphalt," *Engineering and Technical Journal* 29(10):2044-59 (2011); DelRio-Prat et al., "Energy Consumption During Compaction with a Gyratory Intensive Compactor Tester. Estimation Models," *Construction and Building Materials* 25(2): 979-86 (2011); Faheem et al., "Estimating Results of a Proposed Simple Performance Test for Hot-Mix Asphalt from Superpave Gyratory Compactor Results," *Transportation Research Record: Journal of the Transportation Research Board* 1929:104-13 (2005); Mo et al. "Laboratory Investigation of Compaction Characteristics and Performance of Warm Mix Asphalt Containing Chemical Additives," *Construction and Building Materials* 37:239-47 (2012); Sanchez-Alonso et al., "Evaluation of Compactability and Mechanical Properties of Bituminous Mixes with Warm Additives," *Construction and Building Materials* 25(5):2304-1 (2011), all of which are hereby incorporated by reference in its entirety.

In an embodiment of the present invention, asphalt and the epoxidized fatty acid ester may be combined with bio-oil to form a substantially homogeneous mixture. The homogenous material can be graded according to AASHTO MP3 and used as an asphalt binder in paving projects.

The epoxidized fatty acid ester additive, when combined with asphalt, may produce a shear energy of between 0.1 and 100 kJ/m$^2$, and more particularly between 0.1 and 10 kJ/m$^2$. For example, the shear energy of the improved asphalt may be, but is not limited to, 3.48, 2.96, 2.91, 3.93, 3.96, 3.97, 4.8114, 4.5883, 4.4823, or 4.7692 kJ/m². Moreover, the compaction force index may be between 100 and 5,000, and more particularly between 500 and 2,000. For example, the compaction force index may be, but is not limited to, 818.7, 924.1, 1150, 1241.7, 1258, 1350.3, 1456, 1559, 1569, or 1613.3. The number of gyrations to achieve 7% air voids in the epoxidized fatty acid ester with asphalt can range from 25 to 200. For example, the number of gyrations can be, but is not limited to, 43, 49, 58, 68, 80, 111, 193, or 200. In one particular embodiment, the improved asphalt has a minimum compaction force index of 600 at a temperature ranging from 100° C. to 140° C. In another embodiment, the improved asphalt has a maximum compaction force index of 1050 at a temperature ranging from 100° C. to 140° C. Alternatively, the improved asphalt may have a minimum compaction force index of 1050 at a temperature ranging from 100° C. to 140° C. The asphalt may have a maximum compaction force index of 1650 at a temperature ranging from 100° C. to 140° C.

The benefits of this technology include a low cost, efficient, and environmentally-friendly asphalt composition that performs better than currently known asphalt compositions. Further, the epoxidized fatty acid ester additive lowers hot mix asphalt plant production temperatures and acts as a WMA, thus reducing plant emissions. Lastly, the asphalt composition represents the development of green materials/technology that are renewable, and lessen the reliance on foreign crude oil.

Another aspect of the present invention relates to a method of producing an improved polymer modified asphalt. The method involves providing an improved polymer modified asphalt and providing a compound of formula (IIa) or formula (IIb)

(IIa)

MeO—O—... (structure)

(IIb)

MeO—O—... (structure)

The polymer modified asphalt is mixed with the compound of formula (IIa) or formula (IIb) under conditions effective to produce an improved polymer modified asphalt.

Both neat (unmodified) asphalt and polymer modified asphalt binders are used in highway paving applications. As used herein, polymer modified asphalt binders are used on higher volume/loading locations whereas unmodified asphalt binders are used in lower or intermediate volume/loading locations. The use of warm mix asphalt additives have been shown to be successfully used, e.g. improving the compactability, in unmodified asphalt binders. However, warm mix asphalt additives have historically shown limited compactability value for polymer modified asphalt binders.

The compounds of formula (IIa) or formula (IIb) according to the present aspect include epoxidized methyl soyate and may be hydrogenated, as described above.

According to the present invention, the improved asphalt may have a minimum compaction force index of 975 at a temperature ranging from 100° C. to 140° C. The asphalt may have a maximum compaction force index of 1500 at a temperature ranging from 100° C. to 140° C. Compaction energy may be evaluated through use of a Pine AFG2 gyratory compactor and may include moment, height, pressure, and angle of gyration, as described in the previous aspect of the present invention.

Another aspect of the invention relates to an improved asphalt product. The improved asphalt product includes an asphalt and a compound of formula (I)

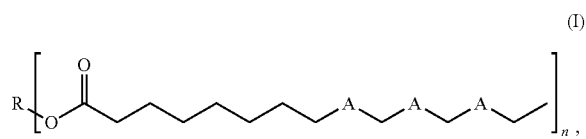

wherein:

each A is selected independently at each occurrence thereof from the group consisting of

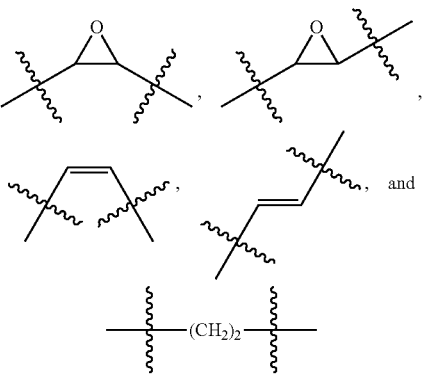

and wherein at least one A is

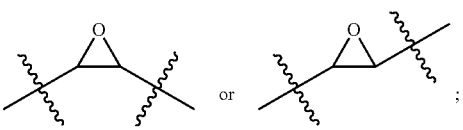 [SMILES: *C1OC1* ; *C1OC1*]

each

represents the point of attachment to a —CH$_2$— group;

n is 1, 2, or 3;

R is selected from the group consisting of H, C$_1$-C$_{23}$ alkyl, and benzyl, wherein the C$_1$-C$_{23}$ alkyl can be optionally substituted with an aryl, heteroaryl, or heterocyclyl; or R is selected from the group consisting of

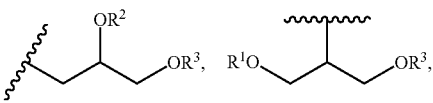

-continued

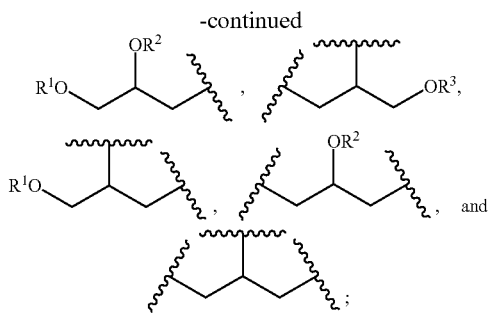

each

represents the point of attachment to a

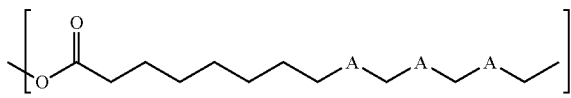

moiety;

$R^1$, $R^2$, and $R^3$ are independently selected from the group consisting of —H and —C(O)$R^4$;

$R^4$ is H, $C_1$-$C_{23}$ alkyl, or aryl, mixed with the asphalt.

The asphalt and epoxidized fatty acid ester used in this aspect of the present invention are described above.

In one embodiment of the present invention, the asphalt product further includes a mineral aggregate. A mineral aggregate may be added to the asphalt product to modify its rheology and temperature susceptibility. In an alternative embodiment, the asphalt product includes asphalt concrete used in pavement. The asphalt binder is mixed with mineral aggregate typically composed of sand, gravel, limestone, crushed stone, slag, and mixtures thereof. The mineral aggregate particles of the present invention include calcium based aggregates, for example, limestone, siliceous based aggregates and mixtures thereof. Aggregates can be selected for asphalt paving applications based on a number of criteria, including physical properties, compatibility with the bitumen to be used in the construction process, availability, and ability to provide a finished pavement that meets the performance specifications of the pavement layer for the traffic projected over the design life of the project.

In one embodiment, the asphalt product is in the form of an asphalt mixture. The asphalt mixture may further include fiberglass and a mineral aggregate including at least one of lime dust and granular ceramic material. Mineral aggregates of the present invention may include elements of less than 0.063 mm and optionally aggregates originating from recycled materials, sand with grain sizes between 0.063 mm and 2 mm and optionally grit, containing grains of a size greater than 2 mm, and optionally alumino-silicates. Aluminosilicates are inorganic compounds based on aluminium and sodium silicates or other metal such as potassium or calcium silicates. Aluminosilicates reduce the viscosity of the warm-mix and are in the form of a powder and/or granulates. The term granulates refers to mineral and/or synthetic granulates, especially coated material aggregates, which are conventionally added to bituminous binders for making mixtures of materials for road construction.

In another embodiment, the asphalt material is used in roofing shingles. For a roofing-grade asphalt material, roofing granules can be applied to a surface of a coated base material. The roofing granules can be used for ultraviolet radiation protection, coloration, impact resistance, fire resistance, another suitable purpose, or any combination thereof. The roofing granules can include inert base particles that are durable, inert inorganic mineral particles, such as andesite, boehmite, coal slag, diabase, metabasalt, nephaline syenite, quartzite, rhyodacite, rhyolite, river gravel, mullite-containing granules, another suitable inert material, or any combination thereof. See U.S. Patent Publ. No. 2013/0160674 to Hong et al., which is hereby incorporated by reference in its entirety.

Roofing granules may also include one or more surface coatings over the shingle. The surface coating can cover at least approximately 75% of the surface of the shingle, and may cover at least approximately 90% of the surface of the shingle and may or may not have a uniform thickness. If more than one surface coating is used, a surface coating closer to the shingle can include a binder that can be inorganic or organic. An inorganic binder can include a silicate binder, a titanate binder, a zirconate binder, an aluminate binder, a phosphate binder, a silica binder, another suitable inorganic binder, or any combination thereof. An organic binder can include a polymeric compound. In a particular embodiment, an organic binder can include an acrylic latex, polyurethane, polyester, silicone, polyamide, or any combination thereof. One or more additional organic binders of the same or different composition can be used.

A surface coating may also or alternatively include a solar reflective material that helps to reflect at least some of the solar energy. For example, UV radiation can further polymerize or harden the asphalt within roofing product being fabricated. A solar reflective material can include titanium dioxide, zinc oxide, or the like. Alternatively, the solar reflective material can include a polymeric material. In one embodiment, a polymer can include a benzene-modified polymer (e.g., copolymer including a styrene and an acrylate), a fluoropolymer, or any combination thereof. Other solar reflective materials are described in U.S. Pat. No. 7,241,500 to Shiao et al. and U.S. Publ. Nos. 2005/0072110 to Shiao et al. and 2008/0220167 to Wisniewski et al., all of which are incorporated by reference for their teachings of materials that are used to reflect radiation (e.g., UV, infrared, etc.) from the sun.

A surface coating can also or alternatively include an algaecide or another biocide to help reduce or delay the formation of algae or another organic growth. The algaecide or other biocide can include an organic or inorganic material. The algaecide or other biocide can include a triazine, a carbamate, an amide, an alcohol, a glycol, a thiazolin, a sulfate, a chloride, copper, a copper compound, zinc, a zinc compound, another suitable biocide, or any combination thereof. In a particular embodiment, the algaecide or other biocide can be included within a polymeric binder. The polymeric binder can include polyethylene, another polyolefin, an acid-containing polyolefin, ethylene vinyl acetate, an ethylene-alkyl acrylate copolymer, a polyvinylbutyral, polyamide, a fluoropolymer, an acrylic, a methacrylate, an acrylate, polyurethane, another suitable binder material, or any combination thereof. The algaecide or other biocide can be an inorganic material that is included within an inorganic binder, for example, within an alkali metal silicate binder. An exemplary inorganic algaecide or other biocide can include a metal (by itself), a metal oxide, a metal salt, or any combination thereof. The metallic element used within the metal, metal oxide, or salt may include copper, zinc, silver, or the like. The metal salt can include a metal sulfate, a metal phosphate, or the like.

A surface coating can include a colorant or another material to provide a desired optical effect. The colorant or other material can include a metal oxide compound, such as titanium dioxide (white), zinc ferrite (yellow), red iron oxides, chrome oxide (green), and ultramarine (blue), silver oxide (black), zinc oxide (dark green), or the like. In another embodiment, the colorant or other material may not be a metal-oxide compound. For example, the colorant may include carbon black, zinc or aluminum flake, or a metal nitride.

The asphalt containing the WMA reaction product is mixed with fiberglass and mineral aggregate typically composed of lime dust and/or granular ceramic material, such as manufactured ceramic material to form roofing shingles. The shingles can also include manufactured sand, e.g., crushed and washed mined aggregate, and also a blend of ceramic material and manufactured sand. The roofing shingles can also include modified asphalt containing a Fischer-Tropsch wax, polyethylene wax, and/or oxidized polyethylene wax. Wax modifiers that can be usefully employed in the context of the present invention include, but are not limited to, waxes of vegetable (e.g. carnuba wax), animal (e.g beeswax) mineral (e.g. Montan™ wax from coal, Fischer Tropsch wax from coal) or petroleum (e.g. paraffin wax, polyethylene wax, Fischer-Tropsch wax from gas) origin including oxidized waxes; amide waxes (e.g. ethylene bis stearamide, stearyl amide, stearyl stearamide); fatty acids and soaps of waxy nature (e.g., aluminum stearate, calcium stearate, fatty acids); other fatty materials of waxy nature (fatty alcohols, hydrogenated fats, fatty esters etc) with the ability to stiffen asphalt, and the like. The above products are basically soluble in the asphalt at warm mix temperatures, to make a homogeneous binder, and/or will melt at the temperature of the mix and the ingredients will disperse/dissolve into the mixture. The wax and resin ingredients will generally act to improve cohesion properties of the asphalt, while the adhesion promoter will improve the adhesion of the asphalt to the aggregate. Together the ingredients provide improved resistance to water damage. The present invention may employ a Fischer Tropsch Wax derived from coal or natural gas or any petroleum feedstock. The process entails the gasification of the above feedstock by partial oxidation to produce carbon monoxide under high temperature and pressure and reaction of the resultant carbon monoxide with hydrogen under high temperature and pressure in the presence of a suitable catalyst (such as iron compound or cobalt compound) for example as in the case of processes employed by Shell and Sasol. The congealing point of the wax is between 68° C. and 120° C. with a Brookfield viscosity at 135° C. in the range of 8 to 20 cPs. For example, the congealing point of the wax may be between 80° C. and 120° C. Alternatively, the congealing point of the wax may be between 68° C. and 105° C. See U.S. Patent Publ. No. 2013/0186302 to Naidoo et al., which is hereby incorporated by reference in its entirety.

A further aspect of the present invention relates to a polymer modified asphalt product. The product includes a polymer modified asphalt and a compound of formula (IIa) or formula (IIb)

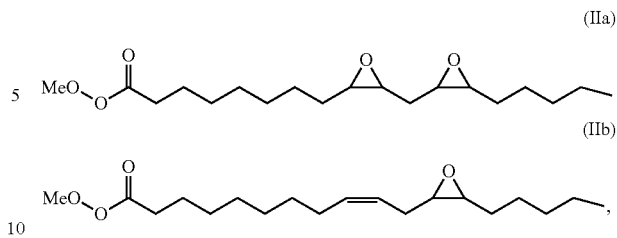

mixed with the improved polymer modified asphalt.

This aspect of the invention is in accordance with the previously described aspects of the invention.

A further aspect of the present invention relates to a method of making an asphalt material. The method includes providing an improved asphalt product comprising an asphalt and a compound of formula (I)

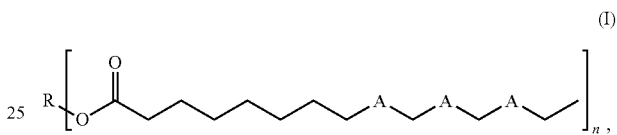

wherein:

each A is selected independently at each occurrence thereof from the group consisting of

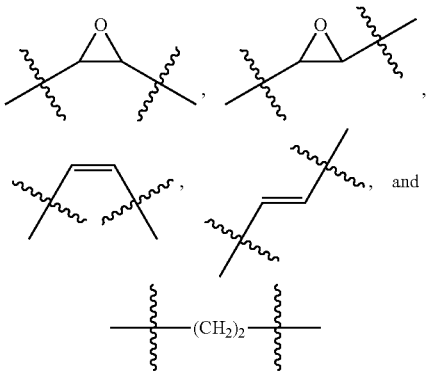

and wherein at least one A is

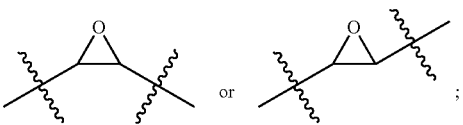 [SMILES: *C1OC1* ; *C1OC1*]

each

represents the point of attachment to a —CH$_2$— group;

n is 1, 2, or 3;

R is selected from the group consisting of H, C$_1$-C$_{23}$ alkyl, and benzyl, wherein the C$_1$-C$_{23}$ alkyl can be optionally substituted with an aryl, heteroaryl, or heterocyclyl; or R is selected from the group consisting of

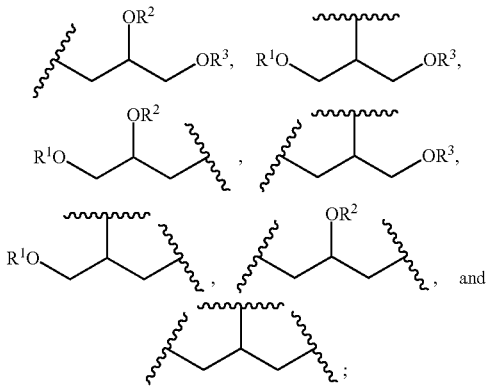

each

represents the point of attachment to a

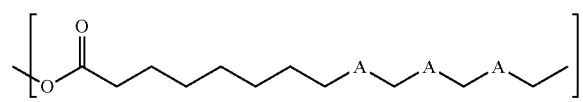

moiety;

R$^1$, R$^2$, and R$^3$ are independently selected from the group consisting of —H and —C(O)R$^4$;

R$^4$ is H, C$_1$-C$_{23}$ alkyl, or aryl, mixed with the asphalt. The method further includes mixing the improved asphalt product with a mineral aggregate at a temperature of 150° C. or lower, to coat the mineral aggregate and produce a heated paving material which, at a warm mix temperature, has a compaction production temperature at least 15-50° C. lower than that produced when the improved asphalt material is prepared in the absence of the compound of formula (I). The heated paving material is applied to a surface to be paved to form an applied paving material. The applied paving material is compacted to a void fraction of less than 8%, at a compacting temperature of 140° C. or lower to form a paved surface.

The asphalt and epoxidized fatty acid ester of this aspect of the present invention are in accordance with the previously described aspects. In one embodiment, the asphalt used in carrying out this aspect of the present invention may be the above described polymer modified asphalt.

The mixing step may be carried out at a temperature of, for example, 150° C., 140° C., 130° C., 120° C., 110° C., 100° C., 90° C., 80° C., 70° C., 60° C., 50° C., 40° C., 30° C., 20° C., 10° C., 5° C., 4° C., 3° C., 2° C., 1° C., or any temperature in between. In one embodiment, mixing is carried out at 110-140° C.

The compacting step may be carried out at a temperature of, for example, 140° C., 130° C., 120° C., 110° C., 100° C., 90° C., 80° C., 70° C., 60° C., 50° C., 40° C., 30° C., 20° C., 10° C., 9° C., 8° C., 7° C., 6° C., 5° C., 4° C., 3° C., 2° C., 1° C., or any temperature in between. In one embodiment, the compacting is carried out at 100-130° C.

The present invention further relates to the asphalt material product of this method. In one embodiment, the asphalt material can be mixed with water and a surfactant and mechanically agitated, in for example, a shear mill, to form an emulsion. Suitable emulsion-forming surfactants are known to those of skill in the art. The emulsified asphalt material can be used as weather-proofing sealant or as an adhesive bonding layer between two surfaces.

The fracture energy of the asphalt material product of the present aspect may be between 5% to 100% greater than that of the improved asphalt material without the epoxidized fatty acid ester. For example, the fracture energy may be 5%, 10%, 15%, 20%, 25%, 30%, 35%, 40%, 45%, 50%, 55%, 60%, 65%, 70%, 75%, 80%, 85%, 90%, 95%, or even 100% greater than when the epoxidized fatty acid ester is present in the asphalt material. In one embodiment, the asphalt material product has a fracture energy, at a temperature ranging from −24 to −6° C., between 10% and 50% greater than that of the improved asphalt material absent the epoxidized fatty acid ester. A semi-circular bend (SCB) test carried out in accordance with AASHTO TP 105-13 is one method for determining fracture energy and may be used herein. See Chong et al., "New Specimen for Fracture Toughness Determination for Rock and Other Materials," *International Journal of Fracture* 26(2): R59-R62 (1984); *Semi-Circular Bending Test: A Practical Crack Growth Test Using Asphalt Concrete Cores*. RILEM PROCEEDINGS, CHAPMAN & HALL (1996); Li et al., "Using Semi Circular Bending Test to Evaluate Low Temperature Fracture Resistance for Asphalt Concrete," *Experimental Mechanics* 50(7):867-76 (2010); Li et al., "Evaluation of the Low Temperature Fracture Resistance of Asphalt Mixtures Using the Semi Circular Bend Test (with Discussion)," *Journal of the Association of Asphalt Paving Technologists* 73 (2004); Lim et al., "Stress Intensity Factors for Semi-Circular Specimens under Three-Point Bending," *Engineering Fracture Mechanics* 44(3):363-82 (1993); Marasteanu et al., "National Pooled Fund Study—Phase Ii: Final Report—Investigations of Low Temperature Cracking in Asphalt Pavements," MN/RC 2012-23, (2012); *Low Temperature Fracture Test for Asphalt Mixtures*. Fifth International RILEM Conference on Reflective Cracking in Pavements (2004) RILEM Publications SARL; and Teshale et al., "Low-Temperature Fracture Behavior of Asphalt Concrete in Semi-Circular Bend Test," University of Minnesota (2012), all of which are hereby incorporated by reference in their entirety.

The stiffness of the asphalt material product of the present aspect may be between 5% to 100% less than that of an asphalt material without the epoxidized fatty acid ester. For example, the stiffness may be 5%, 10%, 15%, 20%, 25%, 30%, 35%, 40%, 45%, 50%, 55%, 60%, 65%, 70%, 75%, 80%, 85%, 90%, 95%, or even 100% less than when the epoxidized fatty acid ester is absent from the asphalt material. In one embodiment, the asphalt material product has a stiffness at a temperature ranging from −24° C. to −6° C., that is reduced by 10% to 30% compared to that of the improved asphalt material absent the epoxidized fatty acid ester. A semi-circular bend (SCB) test carried out in accordance with AASHTO TP 105-13 is one method for determining stiffness and may be used herein.

The Hamburg Steel Wheel Test Stripping Inflection Point may be increased by 1% to 90% compared to that of the improved asphalt material product absent the epoxidized fatty acid ester. For example, the Hamburg Steel Wheel Test Stripping Inflection Point may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, or even 90% higher than when the epoxidized fatty acid ester is absent from the asphalt material. In one embodiment, the asphalt material product has a Hamburg Steel Wheel Test Stripping Inflection Point that is increased by 2% to 40% compared to that of the improved asphalt material absent the epoxidized fatty acid ester. The Hamburg Steel Wheel Tester (HSWT) may be carried out in accordance with AASHTO T324. See AASHTO. T 324—Hamburg Wheel-Track Testing of Compacted Hot Mix Asphalt (HMA) AASHTO T 324-11. Washington, D.C.: American Association of State Highway and Transportation Officials (2011), which is incorporated by reference in its entirety.

The above disclosure generally describes the present invention. A more specific description is provided below in the following examples. The examples are described solely for the purpose of illustration and are not intended to limit the scope of the present invention. Changes in form and substitution of equivalents are contemplated as circumstances suggest or render expedient. Although specific terms have been employed herein, such terms are intended in a descriptive sense and not for purposes of limitation.

EXAMPLES

Example 1—Epoxidized Methyl Soyate

Description of Blend Ingredients—For laboratory testing, an unmodified Montana crude source asphalt supplied by Jebro, with a performance grade ("PG") of 58-28 was used as a first binder while a polymer modified form of this binder was used as a second binder—the PG 58-28 binder polymer modified with 1.5% styrene-butadiene-styrene (SBS) was used to make the PG 64-28 binder. The polymer modified PG 64-28 was blended by the binder supplier. The WMA additive was epoxidized methyl soyate supplied by Archer Daniels Midland (Decatur, Ill.).

To construct the test specimens that make up one half of each HWTD test specimen, a 10 million ESAL design level surface mix approved by the Iowa Department of Transportation (DOT) was used. Each specimen was procured with air voids at 7%±1%, diameter 150 mm and a set height of 61±1 mm. Each individual aggregate's gradation, the blended aggregate gradation, and source information used to produce this mix design are shown in Table 1. The Iowa DOT job mix formula was also verified for each source aggregate's gradation in the laboratory.

TABLE 1

Mix Design Gradation and Supplier Information

| | | Source | | | | | | |
|---|---|---|---|---|---|---|---|---|
| | | Martin Marietta (Ames) | Martin Marietta (Ames) | Oldcastle Materials Group (Johnston) Aggregate | Hallet (Ames) | Martin Marietta (Ames) | Martin Marietta (Ames) | |
| U.S. Sieve | Sieve, mm | 12.5 mm Limestone 29% % Passing | 9.5 mm Limestone 16% % Passing | Quartize 15% % Passing | Natural Sand 13% % Passing | Manuf. Sand 15% % Passing | Agg Lime 12% % Passing | Blend 100% % Passing |
| ¾" | 19 | 100.0 | 100.0 | 100.0 | 100.0 | 100.0 | 100.0 | 100.0 |
| ½" | 12.5 | 79.7 | 100.0 | 100.0 | 100.0 | 100.0 | 100.0 | 94.1 |
| ⅜" | 9.5 | 65.8 | 90.1 | 71.5 | 100.0 | 100.0 | 100.0 | 84.2 |
| #4 | 4.75 | 37.2 | 20.5 | 5.1 | 96.8 | 95.2 | 99 | 53.6 |
| #8 | 2.36 | 18.1 | 2.1 | 2.2 | 64.2 | 65.5 | 97 | 35.7 |
| #16 | 1.18 | 12.5 | 0.7 | 2.0 | 33.7 | 36.3 | 75 | 22.9 |
| #30 | 0.60 | 9.5 | 0.4 | 1.9 | 11.4 | 17.4 | 53 | 13.6 |
| #50 | 0.30 | 7.5 | 0.3 | 1.9 | 0.9 | 6.5 | 38 | 8.2 |
| #100 | 0.15 | 6.2 | 0.3 | 1.5 | 0.1 | 1.9 | 29 | 5.8 |
| #200 | 0.075 | 5.2 | 0.3 | 1.2 | 0.0 | 0.8 | 22.3 | 4.5 |

Methods—Binder rheology testing was completed according to industry standard testing, which is further described in Table 2, below.

TABLE 2

List of Standards Used in Binder Rheology Testing

| Test Name | Aging | Standard Designation | Title | Specified for Grading |
|---|---|---|---|---|
| Dynamic Shear Rheometer (DSR) | Original, Short Term, Long Term | AASHTO T 315-10 | Determining the Rheological Properties of Asphalt Binder Using a Dynamic Shear Rheometer (DSR) | Yes |

TABLE 2-continued

List of Standards Used in Binder Rheology Testing

| Test Name | Aging | Standard Designation | Title | Specified for Grading |
|---|---|---|---|---|
| Rotational Viscometer (RV) | Original | AASHTO T 316-13 | Viscosity Determination of Asphalt Binder Using Rotational Viscometer | Yes |
| Specific Gravity of Asphalt Binder | Original | ASTM D70-09 | Standard Test Method for Density of Semi-Solid Bituminous Materials (Pycnometer Method) | No |
| Separation Tendency | Original | ASTM D7173 - 14 | Standard Practice for Determining the Separation Tendency of Polymer from Polymer Modified Asphalt | No |
| Rolling Thin Film Oven (RTFO) | Short Term | AASHTO T 240-13 | Effect of Heat and Air on a Moving Film of Asphalt Binder (Rolling Thin-Film Oven Test) | Yes |
| Multiple Stress Creep Recovery (MSCR) | Short Term | AASHTO MP 19-10 & AASHTO TP 70-13 | Performance-Graded Asphalt Binder Using Multiple Stress Creep Recovery (MSCR) Test & Multiple Stress Creep Recovery (MSCR) Test of Asphalt Binder Using a Dynamic Shear Rheometer (DSR) | No |
| Pressure Aging Vessel (PAV) | Long Term | AASHTO R 28-12 | Accelerated Aging of Asphalt Binder Using a Pressurized Aging Vessel (PAV) | Yes |
| Bending Beam Rheometer (BBR) | Long Term | AASHTO R 49-09 | Determination of Low-Temperature Performance Grade (PG) of Asphalt Binders | Yes |

The epoxidized methyl soyate (EMS) was blended with the unmodified and polymer modified asphalt with a Silverson shear mill at 140° C. at 3000 rpm for one hour. The dosage levels chosen were 0.5%, and 0.75% for addition of each of the EMS. For example, the EMS was blended at 0.5% by total weight of the total blend and at 0.75% by total weight of the total blend.

The developed blends were then tested in accordance with ASTM and/or AASHTO as described above in Table 2 for viscosity, specific gravity, mass loss, performance grade, and separation. Binder testing included specific gravity, dynamic shear rheometer (DSR) testing on original and aged binders as well as bending beam rheometer tests. Aging included both rolling thin film oven (RTFO) and pressure aging vessel (PAV) aging which simulate short and long term aging of the asphalt, respectively. Mass loss of the binder was measured after RTFO testing. All binder testing followed the American Association of State Highway and Transportation Officials (AASHTO) M320 standard. Asphalt mix testing included moisture sensitivity testing and rutting at high temperature using the Hamburg Wheel Tracking test, and low temperature testing using the Semi-circular Bend test to determine the resistance to cracking/fatigue. Table 3 contains the data for the EMS.

TABLE 3

Summary of Results for Asphalt Binders Modified with EMS

| | Binder | | | | |
|---|---|---|---|---|---|
| | PG 58-28 | PG 58-28 | PG 58-28 | PG 64-28 | PG 64-28 |
| Modifier Dosage (%) | 0 | 0.5 | 0.75 | 0 | 0.75 |
| Failure Temperatures of Original Binder DSR (° C.) | 60.03 | 60.20 | 60.10 | 67.08 | 66.02 |
| Failure Temperatures of RTFO Aged Binder DSR (° C.) | 62.54 | 61.40 | 60.02 | 66.48 | 64.95 |
| Low Temperature Results using the BBR (° C.) | −29.91 | −30.14 | −31.72 | N/T | N/T |
| Performance Grade of Modified Binder | 58-28 | 58-28 | 58-28 | N/T | N/T |
| Specific Gravity | 1.019 | 1.030 | 1.018 | 1.048 | 1.029 |
| Viscosity (Pa*s) at 135° C. | 0.329 | 0.300 | 0.305 | 0.7175 | 0.6725 |
| Viscosity (Pa*s) at 150° C. | 0.172 | 0.184 | 0.191 | 0.385 | 0.355 |
| Viscosity (Pa*s) at 165° C. | 0.107 | 0.140 | 0.148 | 0.2292 | 0.215 |
| Mass Loss (%) | 0.82 | 1.15 | 1.01 | 1.01 | 1.01 |
| Separation | Pass | Pass | Pass | Pass | Pass |

N/T is not tested.

Results—

The data in Table 3 shows that the EMS provides a lower stiffness at the lower temperatures tested for viscosity and performance grading in the dynamic shear rheometer and bending beam rheometer. The specific gravity of the blends did not change from the base asphalts. The mass loss due to the EMS demonstrated there was not a concern. The separation testing demonstrated the EMS did not separate after blending with the asphalt binders.

The developed blends of the EMS and asphalt binders (unmodified and polymer modified) at the 0.75% EMS addition rate were then subsequently mixed with aggregate from Martin Marietta (Ames, Iowa), Hallett Materials (Ames, Iowa), Manatts (Ames, Iowa), and OldCastle Materials Group (Johnston, Iowa) at approximately 5% by total weight of the mix. The samples were compacted as summarized in Table 4.

TABLE 4

Summary of Results for Mix Testing with EMS Modified Asphalt Binders

| | Binder | | | | | |
|---|---|---|---|---|---|---|
| | PG 58-28 WMA | PG 58-28 HMA | PG 58-28 WMA | PG 64-28 WMA | PG 64-28 HMA | PG 64-28 WMA |
| Modifier Dosage (%) | 0 | 0 | 0.75 | 0 | 0 | 0.75 |
| # Gyrations to achieve 7% Air Voids | 58 | 49 | 43 | 80 | 111 | 68 |
| Shear Energy (kJ/m^2) | 3.48 | 2.96 | 2.91 | 3.97 | 3.96 | 3.93 |
| Compaction Force Index | 1150 | 924.1 | 818.7 | 1350.3 | 1613.3 | 1241.7 |
| SCB (AASHTO TP105) (kJ/m^2) | N/T | 1.93 | 2.54 | N/T | N/T | N/T |
| DCT (ASTM D7317) (J/m^2) | 451.9 | 398.4 | 408.3 | 502.4 | 475.7 | 446.4 |
| HSWT (AASHTO T324) SIP (Stripping Inflection Point) | 2327 | 6374 | 2586 | 3560 | 8286 | 5645 |

N/T is not tested.

The samples were evaluated during compaction and after compaction for low temperature performance, and moisture sensitivity/stripping with the data presented in Table 2 above. Compaction evaluation data was collected using a Pine AFG2 gyratory compactor and included moment, height, pressure, and angle of gyration for subsequent calculations and evaluation. This included the number of gyrations to achieve 7% air voids, shear energy, and compaction force index. Low temperature testing was done on the samples using the semi-circular bend (SCB) test (AASHTO TP105) and the disk compact tension (DCT) test (ASTM D7317). Moisture susceptibility/stripping evaluation on the samples were with the Hamburg Steel Wheel Tester (HSWT) in accordance with AASHTO T324. See AASHTO. T 324—Hamburg Wheel-Track Testing of Compacted Hot Mix Asphalt (HMA) AASHTO T 324-11. Washington, D.C.: American Association of State Highway and Transportation Officials (2011), which is hereby incorporated by reference in its entirety.

The evaluation of the mix testing shows the EMS has improved compactibility over the control asphalts (unmodified and polymer modified). The EMS blends showed equal or better low temperature performance over the control asphalt binders and the comparative examples in the SCB and DCT test results, respectively. The EMS blends showed improved moisture susceptibility/stripping performance in the HSWT as compared to the base asphalts (unmodified and polymer modified). These mix performance results are summarized in Table 4.

Example 2—Epoxidized Benzyl Soyate

Description of Blend Ingredients—

For laboratory testing, an unmodified Montana crude source asphalt supplied by Jebro, with a performance grade ("PG") of 58-28 was used as a first binder while a polymer modified form of this binder was used as a second binder—the PG 58-28 binder polymer modified with 1.5% styrene-butadiene-styrene (SBS) was used to make the PG 64-28 binder. The polymer modified PG 64-28 was blended by the binder supplier. The WMA additive was an epoxidized benzyl soyate supplied by Archer Daniels Midland (Decatur, Ill.).

Methods—

The epoxidized benzyl soyate (EBS) was blended with the unmodified and polymer modified asphalt with a Silverson shear mill at 140° C. at 3000 rpm for one hour. The dosage level chosen was 0.75% for addition of each EBS. For example, the EBS was blended at 0.75% by total weight of the total blend.

The developed blends were then tested in accordance with ASTM and/or AASHTO for viscosity, specific gravity, mass loss, performance grade, and separation. Table 5 contains the data for the EBS.

TABLE 5

Summary of Results for Asphalt Binders Modified with EBS

| | Binder | | | |
|---|---|---|---|---|
| | PG 58-28 | PG 58-28 | PG 64-28 | PG 64-28 |
| Modifier Dosage (%) | 0 | 0.75 | 0 | 0.75 |
| Failure Temperatures of Original Binder DSR (° C.) | 60.03 | 40-46 | 67.08 | 46-52 |
| Failure Temperatures of RTFO Aged Binder DSR (° C.) | 62.54 | 40-46 | 66.48 | 46-52 |
| Low Temperature Results using the BBR (° C.) | −29.91 | N/T | N/T | N/T |
| Performance Grade of Modified Binder | 58-28 | N/T | N/T | N/T |
| Specific Gravity | 1.019 | 1.02 | 1.048 | 1.022 |
| Viscosity (Pa*s) at 135° C. | 0.329 | 0.1875 | 0.7175 | 0.3808 |
| Viscosity (Pa*s) at 150° C. | 0.172 | 0.1425 | 0.385 | 0.250 |
| Viscosity (Pa*s) at 165° C. | 0.107 | 0.125 | 0.2292 | 0.1933 |
| Mass Loss (%) | 0.82 | 0.99 | 1.01 | 1.00 |
| Separation | Pass | Pass | Pass | Pass |

N/T is not tested.

Results—

This data in Table 5 shows that the EBS provides a lower stiffness at the lower temperatures tested for viscosity and performance grading in the dynamic shear rheometer and bending beam rheometer. The specific gravity of the blends did not change from the base asphalts. The mass loss due to the EBS demonstrated there was not a concern. The separation testing demonstrated the EBS did not separate after blending with the asphalt binders.

The developed blends of the EBS and asphalt binder (polymer modified) at the 0.75% EBS addition rate were then subsequently mixed with aggregate from Martin Marietta (Ames, Iowa), Hallett Materials (Ames, Iowa), Manatts (Ames, Iowa), and OldCastle Materials Group (Johnston, Iowa) at approximately 5% by total weight of the mix. The samples were compacted as summarized below in Table 6.

The samples were evaluated during compaction with the data summarized in Table 6.

TABLE 6

Summary of Results for Mix Testing with EBS Modified Asphalt Binders

| | Binder | | |
|---|---|---|---|
| | PG 64-28 HMA | PG 64-28 WMA | PG 64-28 WMA |
| Modifier Dosage (%) | 0 | 0 | 0.75 |
| # Gyrations to achieve 7% Air Voids | 200 | 200 | 200 |
| Shear Energy (kJ/m^2) | 4.8114 | 4.5883 | 4.4823 |
| Compaction Force Index | 1569 | 1456 | 1559 |

Compaction evaluation data was collected using a Pine AFG2 gyratory compactor and included moment, height, pressure, and angle of gyration for subsequent calculations and evaluation. This included the number of gyrations to achieve 7% air voids, shear energy, and compaction force index.

The evaluation of the mix compaction shows the EMS has improved compactibility over the control asphalt (polymer modified).

Example 3—Epoxidized Soybean Oil

Description of Blend Ingredients—

For laboratory testing, an unmodified Montana crude source asphalt supplied by Jebro, with a performance grade ("PG") of 58-28 was used as a first binder while a polymer modified form of this binder was used as a second binder—the PG 58-28 binder polymer modified with 1.5% styrene-butadiene-styrene (SBS) was used to make the PG 64-28 binder. The polymer modified PG 64-28 was blended by the binder supplier. The WMA additive was an epoxidized soybean oil supplied by Archer Daniels Midland (Decatur, Ill.).

Methods—

The epoxidized soybean oil (ESO) was blended with the unmodified and polymer modified asphalt with a Silverson shear mill at 140° C. at 3000 rpm for one hour. The ESO was blended at 0.75% by total weight of the total blend.

The developed blends were then tested in accordance with ASTM and/or AASHTO for viscosity, specific gravity, mass loss, performance grade, and separation. Table 7 contains the data for the ESO.

TABLE 7

Summary of Results for Asphalt Binders Modified with ESO

| | Binder | | | |
|---|---|---|---|---|
| | PG 58-28 | PG 58-28 | PG 64-28 | PG 64-28 |
| Modifier Dosage (%) | 0 | 0.75 | 0 | 0.75 |
| Failure Temperatures of Original Binder DSR (° C.) | 60.03 | 59.57 | 67.08 | 65.72 |
| Failure Temperatures of RTFO Aged Binder DSR (° C.) | 62.54 | 60.77 | 66.48 | 65.32 |

TABLE 7-continued

Summary of Results for Asphalt Binders Modified with ESO

| | Binder | | | |
|---|---|---|---|---|
| | PG 58-28 | PG 58-28 | PG 64-28 | PG 64-28 |
| Low Temperature Results using the BBR (° C.) | −29.91 | N/T | N/T | N/T |
| Performance Grade of Modified Binder | 58-28 | N/T | N/T | N/T |
| Specific Gravity | 1.019 | 1.023 | 1.048 | 1.019 |
| Viscosity (Pa*s) at 135° C. | 0.329 | 0.3417 | 0.7175 | 0.6325 |
| Viscosity (Pa*s) at 150° C. | 0.172 | 0.2292 | 0.385 | 0.3475 |
| Viscosity (Pa*s) at 165° C. | 0.107 | 0.1508 | 0.2292 | 0.215 |
| Mass Loss (%) | 0.82 | 1.15 | 1.01 | 0.71 |
| Separation | Pass | Pass | Pass | Pass |

N/T is not tested.

Results—

This data in Table 7 shows that the ESO provides a lower stiffness at the lower temperatures tested for viscosity and performance grading in the dynamic shear rheometer and bending beam rheometer. The specific gravity of the blends did not change from the base asphalts. The mass loss due to the ESO demonstrated there was not a concern. The separation testing demonstrated the ESO did not separate after blending with the asphalt binders.

The developed blends of the ESO and asphalt binder (polymer modified) at the 0.75% ESO addition rate were then subsequently mixed with aggregate from Martin Marietta (Ames, Iowa), Hallett Materials (Ames, Iowa), Manatts (Ames, Iowa), and OldCastle Materials Group (Johnston, Iowa) at approximately 5% by total weight of the mix. The samples were compacted as summarized in Table 8.

The samples were evaluated during compaction with the data summarized in Table 8.

TABLE 8

Summary of Results for Mix Testing with ESO Modified Asphalt Binders

| | Binder | | |
|---|---|---|---|
| | PG 64-28 HMA | PG 64-28 WMA | PG 64-28 WMA |
| Modifier Dosage (%) | 0 | 0 | 0.75 |
| # Gyrations to achieve 7% Air Voids | 200 | 200 | 193 |
| Shear Energy (kJ/m^2) | 4.8114 | 4.5883 | 4.7692 |
| Compaction Force Index | 1569 | 1456 | 1258 |

Compaction evaluation data was collected using a Pine AFG2 gyratory compactor and included moment, height, pressure, and angle of gyration for subsequent calculations and evaluation. This included the number of gyrations to achieve 7% air voids, shear energy, and compaction force index.

The evaluation of the mix compaction shows the ESO has improved compactibility over the control asphalt (polymer modified).

Example 4—Epoxidized Isoamyl Soyate

Description of Blend Ingredients—

For laboratory testing, an unmodified Montana crude source asphalt supplied by Jebro, with a performance grade ("PG") of 58-28 was used as a first binder while a polymer modified form of this binder was used as a second binder—the PG 58-28 binder polymer modified with 1.5% styrene-butadiene-styrene (SBS) was used to make a PG 64-28 binder. The polymer modified PG 64-28 was blended by the binder supplier. The WMA additive was an epoxidized isoamyl soyate supplied by Archer Daniels Midland (Decatur, Ill.).

Methods—

The epoxidized isoamyl soyate (EIAS) was blended with the unmodified and polymer modified asphalt with a Silverson shear mill at 140° C. at 3000 rpm for one hour. The EIAS was blended at 0.75% by total weight of the total blend.

The developed blends were then tested in accordance with ASTM and/or AASHTO for viscosity, specific gravity, mass loss, performance grade, and separation. Table 9 contains the data for the EIAS.

TABLE 9

Summary of Results for Asphalt Binders Modified with EIAS

|  | Binder | | | |
| --- | --- | --- | --- | --- |
|  | PG 58-28 | PG 58-28 | PG 64-28 | PG 64-28 |
| Modifier Dosage (%) | 0 | 0.75 | 0 | 0.75 |
| Failure Temperatures of Original Binder DSR (° C.) | 60.03 | 58.86 | 67.08 | 58.99 |
| Failure Temperatures of RTFO Aged Binder DSR (° C.) | 62.54 | 59.71 | 66.48 | 59.92 |
| Low Temperature Results using the BBR (° C.) | −29.91 | N/T | N/T | N/T |
| Performance Grade of Modified Binder | 58-28 | N/T | N/T | N/T |
| Specific Gravity | 1.019 | 1.021 | 1.048 | 1.024 |
| Viscosity (Pa*s) at 135° C. | 0.329 | 0.3075 | 0.7175 | 0.2975 |
| Viscosity (Pa*s) at 150° C. | 0.172 | 0.200 | 0.385 | 0.1775 |
| Viscosity (Pa*s) at 165° C. | 0.107 | 0.1583 | 0.2292 | 0.1275 |
| Mass Loss (%) | 0.82 | 0.86 | 1.01 | 0.85 |
| Separation | Pass | Pass | Pass | Pass |

N/T is not tested.

Results—

This data in Table 9 shows that the EIAS provides a lower stiffness at the lower temperatures tested for viscosity and performance grading in the dynamic shear rheometer and bending beam rheometer. The specific gravity of the blends did not change from the base asphalts. The mass loss due to the EIAS demonstrated there was not a concern. The separation testing demonstrated the EIAS did not separate after blending with the asphalt binders.

Example 5—Epoxidized Corn Oil

Description of Blend Ingredients—

For laboratory testing, an unmodified Montana crude source asphalt supplied by Jebro, with a performance grade ("PG") of 58-28 was used as a first binder while a polymer modified form of this binder was used as a second binder—the PG 58-28 binder polymer modified with 1.5% styrene-butadiene-styrene (SBS) was used to make the PG 64-28 binder. The polymer modified PG 64-28 was blended by the binder supplier. Corn oil was obtained at Hyvee (Ames, Iowa). The epoxidized corn oil was produced at Iowa State University using the aforementioned corn oil.

Methods—

The epoxidized corn oil (ECO) was blended with the unmodified and polymer modified asphalt with a Silverson shear mill at 140° C. at 3000 rpm for one hour. The ECO was blended at 0.75% by total weight of the total blend.

The developed blends were then tested in accordance with ASTM and/or AASHTO for viscosity, specific gravity, mass loss, performance grade, and separation. Table 10 contains the data for the ECO.

TABLE 10

Summary of Results for Asphalt Binders Modified with ECO

|  | Binder | | | |
| --- | --- | --- | --- | --- |
|  | PG 58-28 | PG 58-28 | PG 64-28 | PG 64-28 |
| Modifier Dosage (%) | 0 | 0.75 | 0 | 0.75 |
| Failure Temperatures of Original Binder DSR (° C.) | 60.03 | 59.64 | 67.08 | 65.38 |
| Failure Temperatures of RTFO Aged Binder DSR (° C.) | 62.54 | 60.14 | 66.48 | 65.18 |
| Low Temperature Results using the BBR (° C.) | −29.91 | N/T | N/T | N/T |
| Performance Grade of Modified Binder | 58-28 | N/T | N/T | N/T |
| Specific Gravity | 1.019 | 1.019 | 1.048 | 1.020 |
| Viscosity (Pa*s) at 135° C. | 0.329 | 0.3083 | 0.7175 | 0.660 |
| Viscosity (Pa*s) at 150° C. | 0.172 | 0.1908 | 0.385 | 0.355 |
| Viscosity (Pa*s) at 165° C. | 0.107 | 0.1475 | 0.2292 | 0.215 |
| Mass Loss (%) | 0.82 | 0.85 | 1.01 | 0.85 |
| Separation | Pass | Pass | Pass | Pass |

N/T is not tested.

This data shows that the ECO provides a lower stiffness at the lower temperatures tested for viscosity and performance grading in the dynamic shear rheometer and bending beam rheometer. The specific gravity of the blends did not change from the base asphalts. The mass loss due to the ECO demonstrated there was not a concern. The separation testing demonstrated the ECO did not separate after blending with the asphalt binders.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An asphalt product comprising:

an asphalt and a compound of formula (I)

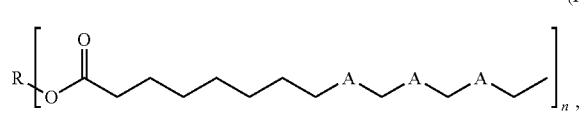

wherein:

each A is selected independently at each occurrence thereof from the group consisting of

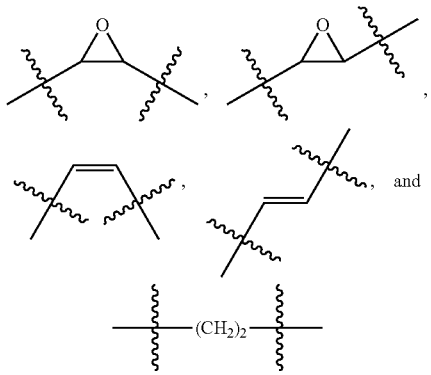

and wherein at least one A is

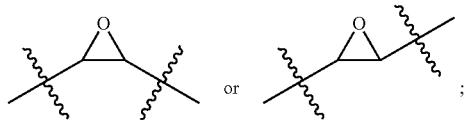 [SMILES: *C1OC1* ; *C1OC1*]

each

represents the point of attachment to a —CH$_2$— group;

n is 1;

R is methyl, wherein the compound of formula (I) is epoxidized methyl soyate and is mixed with the asphalt.

2. The asphalt product of claim 1, wherein the asphalt product has a viscosity of 0.23-0.33 Pa·s at a temperature ranging from 130° C. to 150° C.

3. The asphalt product of claim 1, wherein the asphalt product has a viscosity of 0.13-0.21 Pa·s at a temperature ranging from 150° C. to 165° C.

4. The asphalt product of claim 1 further comprising:

a mineral aggregate, wherein the asphalt product has a minimum compaction force index of 1050 at a temperature ranging from 100° C. to 140° C.

5. The asphalt product of claim 1 further comprising:

a mineral aggregate, wherein the asphalt product has a maximum compaction force index energy of 1650 at a temperature ranging from 100° C. to 140° C.

6. The asphalt product of claim 1 further comprising:

a mineral aggregate.

7. In a roofing shingle, the improvement comprising the asphalt product of claim 1.

8. A method of producing an improved asphalt comprising:

providing an asphalt;

providing a compound of formula (I)

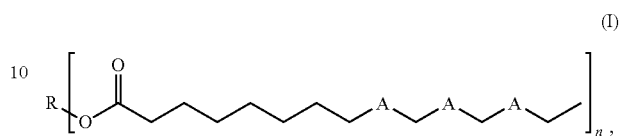

wherein:

each A is selected independently at each occurrence thereof from the group consisting of

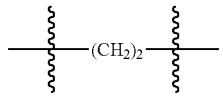

and wherein at least one A is

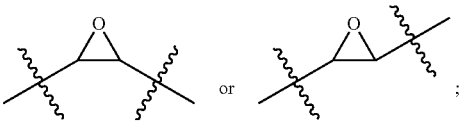 [SMILES: *C1OC1* ; *C1OC1*]

each

represents the point of attachment to a —CH$_2$— group;

n is 1;

R is methyl; and mixing the asphalt with the compound of formula (I), wherein the compound of formula (I) is epoxidized methyl soyate, under conditions effective to produce an improved asphalt.

9. A method of making an asphalt material comprising the steps of:
(a) providing an improved asphalt product comprising:
an asphalt and
a compound of formula (I)

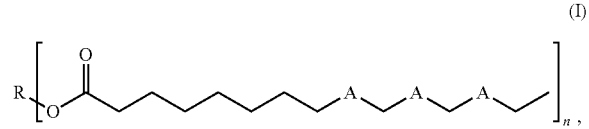

wherein:
each A is selected independently at each occurrence thereof from the group consisting of

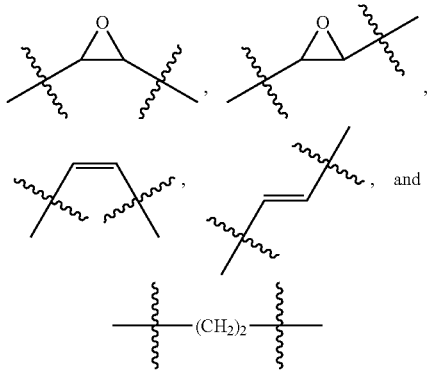

and
wherein at least one A is

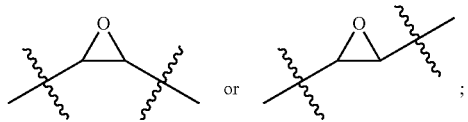 [SMILES: *C1OC1* ; *C1OC1*]

each

represents the point of attachment to a —CH$_2$— group;
n is 1;
R is methyl, wherein the compound of formula (I) is epoxidized methyl soyate;
(b) mixing the improved asphalt product with a mineral aggregate at a temperature of 150° C. or lower, to coat the mineral aggregate and produce a heated paving material which, at a warm mix temperature, has a compaction production temperature at least 15-50° C. lower than that produced when the improved asphalt material is prepared in the absence of the compound of formula (I);
(c) applying the heated paving material to a surface to be paved to form an applied paving material, and
(d) compacting the applied paving material, to a void fraction of less than 8%, at a compacting temperature of 140° C. or lower to form a paved surface.

10. A method of producing an improved polymer modified asphalt comprising:
providing a polymer modified asphalt;
providing epoxidized methyl soyate; and
mixing the polymer modified asphalt with the epoxidized methyl soyate under conditions effective to produce an improved polymer modified asphalt.

11. A polymer modified asphalt product comprising:
a polymer modified asphalt and epoxidized methyl soyate mixed with the polymer modified asphalt.

12. The polymer modified asphalt product of claim 11, wherein the epoxidized methyl soyate is mixed in an amount of 0.1 to 5.0 wt % with the asphalt.

* * * * *